US012564593B2

(12) United States Patent
Parikh et al.

(10) Patent No.: US 12,564,593 B2
(45) Date of Patent: *Mar. 3, 2026

(54) TOPICAL FORMULATION FOR A JAK INHIBITOR

(71) Applicants: Incyte Corporation, Wilmington, DE (US); Incyte Holdings Corporation, Wilmington, DE (US)

(72) Inventors: Bhavnish Parikh, Avondale, PA (US); Bhavesh Shah, San Antonio, TX (US); Krishnaswamy Yeleswaram, Landenberg, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/274,086

(22) Filed: Jul. 18, 2025

(65) Prior Publication Data

US 2025/0345337 A1 Nov. 13, 2025

Related U.S. Application Data

(60) Continuation of application No. 17/541,439, filed on Dec. 3, 2021, which is a continuation of application No. 16/948,408, filed on Sep. 17, 2020, now Pat. No. 11,219,624, which is a continuation of application No. 16/947,735, filed on Aug. 14, 2020, now Pat. No. 10,869,870, which is a division of application No. 16/566,625, filed on Sep. 10, 2019, now Pat. No. 10,758,543, which is a continuation of application No. 14/714,820, filed on May 18, 2015, now abandoned, which is a continuation of application No. 13/112,370, filed on May 20, 2011, now abandoned.

(60) Provisional application No. 61/347,132, filed on May 21, 2010.

(51) Int. Cl.

| | |
|---|---|
| ***A01N 37/00*** | (2006.01) |
| ***A01N 25/00*** | (2006.01) |
| ***A01N 37/12*** | (2006.01) |
| ***A01N 37/44*** | (2006.01) |
| ***A61K 9/00*** | (2006.01) |
| ***A61K 9/06*** | (2006.01) |
| ***A61K 9/107*** | (2006.01) |
| ***A61K 31/215*** | (2006.01) |
| ***A61K 31/24*** | (2006.01) |
| ***A61K 31/519*** | (2006.01) |
| ***A61K 47/06*** | (2006.01) |
| ***A61K 47/10*** | (2017.01) |
| ***A61K 47/14*** | (2017.01) |
| ***A61K 47/24*** | (2006.01) |
| ***A61K 47/26*** | (2006.01) |
| ***A61K 47/36*** | (2006.01) |
| ***A61P 17/00*** | (2006.01) |
| ***A61P 17/06*** | (2006.01) |

(52) U.S. Cl.

CPC .......... *A61K 31/519* (2013.01); *A61K 9/0014* (2013.01); *A61K 9/06* (2013.01); *A61K 9/107* (2013.01); *A61K 47/06* (2013.01); *A61K 47/10* (2013.01); *A61K 47/14* (2013.01); *A61K 47/24* (2013.01); *A61K 47/26* (2013.01); *A61K 47/36* (2013.01); *A61P 17/00* (2018.01); *A61P 17/06* (2018.01)

(58) Field of Classification Search

CPC ..................................................... A61K 31/46

See application file for complete search history.

(56) References Cited

U.S. PATENT DOCUMENTS

| | | | |
|---|---|---|---|
| 2,985,589 | A | 5/1961 | Broughton et al. |
| 3,832,460 | A | 8/1974 | Kosti |
| 4,140,755 | A | 2/1979 | Sheth |
| 4,402,832 | A | 9/1983 | Gerhold |
| 4,498,991 | A | 2/1985 | Oroskar |
| 4,512,984 | A | 4/1985 | Seurfert et al. |
| 4,548,990 | A | 10/1985 | Mueller et al. |
| 4,814,477 | A | 3/1989 | Wijnberg et al. |
| 5,378,700 | A | 1/1995 | Sakuma et al. |
| 5,472,949 | A | 12/1995 | Arasaki |
| 5,510,101 | A | 4/1996 | Stroppolo |
| 5,521,184 | A | 5/1996 | Zimmermann |
| 5,630,943 | A | 5/1997 | Grill |
| 5,702,688 | A | 12/1997 | Yu |
| 5,795,909 | A | 8/1998 | Shashoua et al. |
| 5,856,326 | A | 1/1999 | Anthony |
| 5,919,779 | A | 7/1999 | Proudfoot et al. |
| 6,025,366 | A | 2/2000 | Walsh et al. |

(Continued)

FOREIGN PATENT DOCUMENTS

| | | |
|---|---|---|
| CN | 102026999 | 4/2011 |
| CN | 102458581 | 5/2012 |

(Continued)

OTHER PUBLICATIONS

English Translation of Main Text of Request for Patent Invalidation for Chinese Patent No. ZL201180035301.2, dated Jul. 25, 2025 (69 pages).

(Continued)

*Primary Examiner* — Layla Soroush

(74) *Attorney, Agent, or Firm* — Finnegan, Henderson, Farabow, Garrett & Duner, LLP

(57) ABSTRACT

This invention relates to pharmaceutical formulations for topical skin application comprising (R)-3-cyclopentyl-3-[4-(7H-pyrrolo[2,3-d]pyrimidin-4-yl)-1 H-pyrazol-1-yl]propanenitrile, or a pharmaceutically acceptable salt thereof, and use in the treatment of skin disorders.

23 Claims, 7 Drawing Sheets

(56) References Cited

U.S. PATENT DOCUMENTS

| | | | |
|---|---|---|---|
| 6,060,038 | A | 5/2000 | Burns |
| 6,075,056 | A | 6/2000 | Quigley, Jr. et al. |
| 6,136,198 | A | 10/2000 | Adam et al. |
| 6,217,895 | B1 | 4/2001 | Guo et al. |
| 6,335,342 | B1 | 1/2002 | Longo et al. |
| 6,375,839 | B1 | 4/2002 | Adam et al. |
| 6,413,419 | B1 | 7/2002 | Adam et al. |
| 6,486,322 | B1 | 11/2002 | Longo et al. |
| 6,518,265 | B1 | 2/2003 | Kato et al. |
| 6,548,078 | B2 | 4/2003 | Guo |
| 6,569,443 | B1 | 5/2003 | Dawson |
| 6,579,882 | B2 | 6/2003 | Stewart et al. |
| 6,624,138 | B1 | 9/2003 | Sung et al. |
| 6,635,762 | B1 | 10/2003 | Blumenkopf et al. |
| 6,712,973 | B2 | 3/2004 | Adam et al. |
| 6,713,089 | B1 | 3/2004 | Bertelsen et al. |
| 6,852,727 | B2 | 2/2005 | Goulet et al. |
| 6,953,776 | B2 | 10/2005 | Di Napoli |
| 7,005,436 | B2 | 2/2006 | Lloyd et al. |
| 7,167,750 | B2 | 1/2007 | Knudson et al. |
| 7,265,108 | B2 | 9/2007 | Ozaki |
| 7,335,667 | B2 | 2/2008 | Rodgers et al. |
| 7,358,255 | B2 | 4/2008 | Nakamura |
| 7,517,870 | B2 | 4/2009 | Auricchio |
| 7,598,257 | B2 | 10/2009 | Rodgers et al. |
| 7,683,171 | B2 | 3/2010 | Pitts et al. |
| 7,745,437 | B2 | 6/2010 | Ren et al. |
| 7,750,007 | B2 | 7/2010 | Bearss et al. |
| 7,834,022 | B2 | 11/2010 | Rodgers et al. |
| 8,053,433 | B2 | 11/2011 | Rodgers et al. |
| 8,158,616 | B2 | 4/2012 | Rodgers et al. |
| 8,309,718 | B2 | 11/2012 | Li et al. |
| 8,410,265 | B2 | 4/2013 | Zhou et al. |
| 8,415,362 | B2 | 4/2013 | Rodgers et al. |
| 8,420,629 | B2 | 4/2013 | Rodgers et al. |
| 8,440,679 | B2 | 5/2013 | McAllister |
| 8,445,488 | B2 | 5/2013 | Rodger et al. |
| 8,486,902 | B2 | 7/2013 | Rodgers et al. |
| 8,513,270 | B2 | 8/2013 | Arvanitis et al. |
| 8,530,485 | B2 | 9/2013 | Rodgers et al. |
| 8,541,425 | B2 | 9/2013 | Rodgers et al. |
| 8,563,541 | B2 | 10/2013 | Arvanitis et al. |
| 8,604,043 | B2 | 12/2013 | Li et al. |
| 8,637,529 | B2 | 1/2014 | Woller |
| 8,691,807 | B2 | 4/2014 | Yao et al. |
| 8,715,700 | B2 | 5/2014 | Chang |
| 8,716,303 | B2 | 5/2014 | Rodgers et al. |
| 8,722,693 | B2 | 5/2014 | Rodgers et al. |
| 8,741,895 | B2 | 6/2014 | Rodgers et al. |
| 8,748,401 | B2 | 6/2014 | Rodgers et al. |
| 8,765,734 | B2 | 7/2014 | Huang et al. |
| 8,822,481 | B1 | 9/2014 | Rodgers et al. |
| 8,829,013 | B1 | 9/2014 | Rodgers et al. |
| 8,835,423 | B2 | 9/2014 | Arvanitis et al. |
| 8,841,318 | B2 | 9/2014 | Arvanitis et al. |
| 8,883,806 | B2 | 11/2014 | Zhou et al. |
| 8,889,697 | B2 | 11/2014 | Rodgers et al. |
| 8,933,085 | B2 | 1/2015 | Rodgers et al. |
| 8,933,086 | B2 | 1/2015 | Rodgers et al. |
| 8,946,245 | B2 | 2/2015 | Rodgers et al. |
| 8,987,442 | B2 | 3/2015 | Tung et al. |
| 8,987,443 | B2 | 3/2015 | Liu |
| 8,993,582 | B2 | 3/2015 | Zhou et al. |
| 9,000,161 | B2 | 4/2015 | Zhou et al. |
| 9,023,840 | B2 | 5/2015 | Yao et al. |
| 9,034,884 | B2 | 5/2015 | Rodgers et al. |
| 9,079,912 | B2 | 7/2015 | Rodgers et al. |
| 9,090,611 | B2 | 7/2015 | Rodgers et al. |
| 9,181,271 | B2 | 11/2015 | Li et al. |
| 9,206,187 | B2 | 12/2015 | Rodgers et al. |
| 9,216,984 | B2 | 12/2015 | Li |
| 9,221,845 | B2 | 12/2015 | Cao |
| 9,290,506 | B2 | 3/2016 | Zhou et al. |
| 9,334,274 | B2 | 5/2016 | Rodgers |
| 9,359,358 | B2 | 6/2016 | Rodgers |
| 9,376,439 | B2 | 6/2016 | Rodgers |
| 9,464,088 | B2 | 10/2016 | Huang |
| 9,487,521 | B2 | 11/2016 | Zhou et al. |
| 9,498,467 | B2 | 11/2016 | Leopold et al. |
| 9,611,269 | B2 | 4/2017 | Yao et al. |
| 9,623,029 | B2 | 4/2017 | Li et al. |
| 9,655,854 | B2 | 5/2017 | Yeleswaram |
| 9,974,790 | B2 | 5/2018 | Rodgers et al. |
| 9,999,619 | B2 | 6/2018 | Huang et al. |
| 10,398,699 | B2 | 9/2019 | Rodgers et al. |
| 2002/0111353 | A1 | 8/2002 | Ledeboer et al. |
| 2003/0064969 | A1 | 4/2003 | Bhagwat et al. |
| 2003/0100756 | A1 | 5/2003 | Adams et al. |
| 2003/0144309 | A1 | 7/2003 | Choon-Moon |
| 2003/0165576 | A1 | 9/2003 | Fujii et al. |
| 2004/0009222 | A1 | 1/2004 | Chou et al. |
| 2004/0009983 | A1 | 1/2004 | Cox et al. |
| 2004/0029857 | A1 | 2/2004 | Hale et al. |
| 2004/0077654 | A1 | 4/2004 | Bouillot et al. |
| 2004/0099204 | A1 | 5/2004 | Nestor |
| 2004/0198737 | A1 | 10/2004 | Cox et al. |
| 2004/0204404 | A1 | 10/2004 | Zelle |
| 2004/0214928 | A1 | 10/2004 | Aronov |
| 2004/0235862 | A1 | 11/2004 | Bums |
| 2005/0014966 | A1 | 1/2005 | Tabe |
| 2005/0054568 | A1 | 3/2005 | Ling |
| 2005/0153989 | A1 | 7/2005 | Grotzfeld et al. |
| 2006/0004010 | A1 | 1/2006 | Hahashita et al. |
| 2006/0020011 | A1 | 1/2006 | Wu et al. |
| 2006/0079511 | A1 | 4/2006 | Liu et al. |
| 2006/0106020 | A1 | 5/2006 | Rodgers et al. |
| 2006/0106027 | A1 | 5/2006 | Furet et al. |
| 2006/0128803 | A1 | 6/2006 | Klimko |
| 2006/0135537 | A1 | 6/2006 | Knegtel et al. |
| 2006/0178393 | A1 | 8/2006 | Pitts |
| 2006/0183761 | A1 | 8/2006 | Ledeboer et al. |
| 2006/0183906 | A1 | 8/2006 | Rodgers et al. |
| 2006/0223864 | A1 | 10/2006 | Biju |
| 2006/0293311 | A1 | 12/2006 | Li et al. |
| 2007/0135461 | A1 | 6/2007 | Rodgers et al. |
| 2007/0135466 | A1 | 6/2007 | Ledeboer et al. |
| 2007/0149506 | A1 | 6/2007 | Arvanitis et al. |
| 2007/0149561 | A1 | 6/2007 | Dhanak et al. |
| 2007/0191364 | A1 | 8/2007 | Braun et al. |
| 2007/0191405 | A1 | 8/2007 | Noronha |
| 2007/0208053 | A1 | 9/2007 | Wang et al. |
| 2007/0225286 | A1 | 9/2007 | Ren et al. |
| 2007/0259904 | A1 | 11/2007 | Noronha |
| 2007/0264344 | A1 | 11/2007 | Segura-Orsoni |
| 2008/0021026 | A1 | 1/2008 | Kahraman et al. |
| 2008/0085898 | A1 | 4/2008 | Lu |
| 2008/0096852 | A1 | 4/2008 | Yanni |
| 2008/0119496 | A1 | 5/2008 | Ohlmeyer |
| 2008/0161346 | A1 | 7/2008 | Cheng |
| 2008/0188500 | A1 | 8/2008 | Arvanitis et al. |
| 2008/0194468 | A1 | 8/2008 | Bodor |
| 2008/0207570 | A1 | 8/2008 | Segura-Orsoni |
| 2008/0207584 | A1 | 8/2008 | Habashita et al. |
| 2008/0280876 | A1 | 11/2008 | Hobson et al. |
| 2008/0312258 | A1 | 12/2008 | Rodgers et al. |
| 2008/0312259 | A1 | 12/2008 | Rodgers |
| 2009/0018156 | A1 | 1/2009 | Tang et al. |
| 2009/0076070 | A1 | 3/2009 | Harada et al. |
| 2009/0088445 | A1 | 4/2009 | Ledeboer et al. |
| 2009/0131403 | A1 | 5/2009 | Kusuda |
| 2009/0181959 | A1 | 7/2009 | Rodgers et al. |
| 2009/0197869 | A1 | 8/2009 | Arvanitis et al. |
| 2009/0203637 | A1 | 8/2009 | Hocek et al. |
| 2009/0215766 | A1 | 8/2009 | Rodgers et al. |
| 2009/0221608 | A1 | 9/2009 | Cui et al. |
| 2009/0233903 | A1 | 9/2009 | Rodgers et al. |
| 2009/0318405 | A1 | 12/2009 | Li et al. |
| 2010/0022522 | A1 | 1/2010 | Rodgers et al. |
| 2010/0069381 | A1 | 3/2010 | Itoh et al. |
| 2010/0113416 | A1 | 5/2010 | Friedman et al. |
| 2010/0190981 | A1 | 7/2010 | Zhou et al. |
| 2010/0210627 | A1 | 8/2010 | Mao et al. |
| 2010/0298334 | A1 | 11/2010 | Rodgers et al. |
| 2010/0298355 | A1 | 11/2010 | Li et al. |

(56) References Cited

U.S. PATENT DOCUMENTS

| | | | |
|---|---|---|---|
| 2011/0059951 | A1 | 3/2011 | Rodgers et al. |
| 2011/0082159 | A1 | 4/2011 | Rodgers et al. |
| 2011/0086810 | A1 | 4/2011 | Rodgers et al. |
| 2011/0086835 | A1 | 4/2011 | Rodgers et al. |
| 2011/0201593 | A1 | 8/2011 | Babu et al. |
| 2011/0207754 | A1 | 8/2011 | Li et al. |
| 2011/0223210 | A1 | 9/2011 | Rodgers et al. |
| 2011/0224157 | A1 | 9/2011 | Rodgers et al. |
| 2011/0224190 | A1 | 9/2011 | Huang et al. |
| 2011/0288107 | A1 | 11/2011 | Parikh et al. |
| 2012/0014989 | A1 | 1/2012 | Rodgers |
| 2012/0077798 | A1 | 3/2012 | Rodgers et al. |
| 2012/0149681 | A1 | 6/2012 | Rodgers |
| 2012/0149682 | A1 | 6/2012 | Rodgers et al. |
| 2012/0214825 | A1 | 8/2012 | Vannucchi et al. |
| 2012/0225057 | A1 | 9/2012 | Flynn |
| 2012/0252779 | A1 | 10/2012 | Ramsden |
| 2012/0301464 | A1 | 11/2012 | Friedman et al. |
| 2012/0329782 | A1 | 12/2012 | Arvanitis et al. |
| 2013/0018034 | A1 | 1/2013 | Yao et al. |
| 2013/0040973 | A1 | 2/2013 | Vannucchi et al. |
| 2013/0045963 | A1 | 2/2013 | Rodgers et al. |
| 2013/0060026 | A1 | 3/2013 | Zhou et al. |
| 2013/0137681 | A1 | 5/2013 | Rodgers et al. |
| 2013/0225556 | A1 | 8/2013 | Rodgers et al. |
| 2013/0253190 | A1 | 9/2013 | Zhou et al. |
| 2013/0253191 | A1 | 9/2013 | Zhou et al. |
| 2013/0253193 | A1 | 9/2013 | Zhou et al. |
| 2013/0274257 | A1 | 10/2013 | Arvanitis et al. |
| 2013/0296299 | A1 | 11/2013 | Rodgers et al. |
| 2014/0004516 | A1 | 1/2014 | Sattler et al. |
| 2014/0005166 | A1 | 1/2014 | Rodgers et al. |
| 2014/0005210 | A1 | 1/2014 | Rodgers et al. |
| 2014/0018374 | A1 | 1/2014 | Rodgers et al. |
| 2014/0031344 | A1 | 1/2014 | Arvanitis et al. |
| 2014/0073657 | A1 | 3/2014 | Li et al. |
| 2014/0094477 | A1 | 4/2014 | Rodgers et al. |
| 2014/0121198 | A1 | 5/2014 | Li et al. |
| 2014/0135350 | A1 | 5/2014 | Ni et al. |
| 2014/0171409 | A1 | 6/2014 | Yao et al. |
| 2014/0221379 | A1 | 8/2014 | Rodgers et al. |
| 2014/0228346 | A1 | 8/2014 | Rodgers et al. |
| 2014/0243360 | A1 | 8/2014 | Rodgers et al. |
| 2014/0256941 | A1 | 9/2014 | Liu et al. |
| 2014/0275031 | A1 | 9/2014 | Huang et al. |
| 2014/0303196 | A1 | 10/2014 | Rodgers et al. |
| 2014/0343030 | A1 | 11/2014 | Li et al. |
| 2014/0378400 | A1 | 12/2014 | Rodgers et al. |
| 2015/0065447 | A1 | 3/2015 | Sandor |
| 2015/0065484 | A1 | 3/2015 | Yeleswaram et al. |
| 2015/0087632 | A1 | 3/2015 | Rodgers et al. |
| 2015/0087662 | A1 | 3/2015 | Li et al. |
| 2015/0152117 | A1 | 6/2015 | Gibbons |
| 2015/0164900 | A1 | 6/2015 | Rodgers et al. |
| 2015/0183805 | A1 | 7/2015 | Liu et al. |
| 2015/0225411 | A1 | 8/2015 | Yao et al. |
| 2015/0225412 | A1 | 8/2015 | Brameld |
| 2015/0238492 | A1 | 8/2015 | Rodgers et al. |
| 2015/0246046 | A1 | 9/2015 | Vaddi |
| 2015/0250790 | A1 | 9/2015 | Parikh et al. |
| 2015/0315185 | A1 | 11/2015 | Rodgers et al. |
| 2015/0342952 | A1 | 12/2015 | Leopold |
| 2015/0344497 | A1 | 12/2015 | Zhou et al. |
| 2016/0000795 | A1 | 1/2016 | Scherle |
| 2016/0015695 | A1 | 1/2016 | Li et al. |
| 2016/0024109 | A1 | 1/2016 | Li |
| 2016/0067253 | A1 | 3/2016 | Li et al. |
| 2016/0272648 | A1 | 9/2016 | Rodgers et al. |
| 2016/0346286 | A1 | 12/2016 | Rodgers et al. |
| 2016/0347734 | A1 | 12/2016 | Liu et al. |
| 2017/0015674 | A1 | 1/2017 | Zhou et al. |
| 2017/0071947 | A1 | 3/2017 | Rodgers et al. |
| 2017/0087158 | A1 | 3/2017 | Friedman et al. |
| 2017/0246157 | A1 | 8/2017 | Huang et al. |
| 2017/0253598 | A1 | 9/2017 | Yao et al. |
| 2017/0319487 | A1 | 11/2017 | Yeleswaram et al. |
| 2018/0338978 | A1 | 11/2018 | Rodgers et al. |
| 2018/0353499 | A1 | 12/2018 | Huang et al. |
| 2019/0111058 | A1 | 4/2019 | Vaddi |
| 2019/0125750 | A1 | 5/2019 | Rodgers et al. |
| 2019/0135813 | A1 | 5/2019 | Rodgers et al. |

FOREIGN PATENT DOCUMENTS

| | | |
|---|---|---|
| CN | 102985417 | 3/2013 |
| DE | 3036390 | 5/1982 |
| EP | 0223420 | 5/1987 |
| EP | 0727217 | 8/1996 |
| EP | 0795556 | 9/1997 |
| JP | 07-010876 | 1/1995 |
| JP | 2003-155285 | 5/2003 |
| JP | 2004-531513 | 10/2004 |
| JP | 2006-502183 | 1/2006 |
| JP | 2006-518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| JP | 2011-503194 | 1/2011 |
| JP | 2011-514909 | 5/2011 |
| JP | 2013-522214 | 6/2013 |
| JP | 2013-543007 | 11/2013 |
| MX | 2015005428 | 7/2015 |
| MX | 2015015738 | 3/2016 |
| WO | WO 96/030343 | 10/1996 |
| WO | WO 97/002262 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 2001/081346 | 11/2001 |
| WO | WO 01/098344 | 12/2001 |
| WO | WO 02/000196 | 1/2002 |
| WO | WO 02/000661 | 1/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 2003/000688 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |

(56) References Cited

FOREIGN PATENT DOCUMENTS

| | | |
|---|---|---|
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 2007/044050 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 08/013925 | 1/2008 |
| WO | WO 08/028937 | 3/2008 |
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/1 45688 | 12/2008 |
| WO | WO 08/145681 | 12/2008 |
| WO | WO 08/157207 | 12/2008 |
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/158687 | 12/2009 |
| WO | WO 2009/158687 A1 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 2010/043052 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 12/068450 | 5/2012 |
| WO | WO 12/071612 | 6/2012 |
| WO | WO 12/177606 | 12/2012 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 14/138168 | 9/2014 |
| WO | WO 2014/186706 | 11/2014 |
| WO | WO 2015/184305 | 12/2015 |
| WO | WO 2015/184087 | 4/2018 |

OTHER PUBLICATIONS

English Translation of Main Text of Request for Patent Invalidation for Chinese Patent No. ZL201610207261.X, dated Jul. 25, 2025 (73 pages).

English Translation of Supplementary Opinion by the Petitioner in Invalidation Proceedings for Chinese Patent No. ZL201180035301.2 (Case No. 4W120582), dated Aug. 22, 2025 (7 pages).

Vannucchi, et al., Ruxolitinib versus Standard Therapy for the Treatment of Polycythemia Vera, N Engl J Med. Jan. 29, 2015; 372(5): 426-435.

Eurasian Office Action in Eurasian Application No. 20120013228, Oct. 24, 2019, 4 pages.

National Cancer Institute, "Ruxolitinib Phosphate," Last updated Mar. 9, 2018, retrieved from URL<https://www.cancer.gov/about-cancer/treatment/drugs/ruxolitinibphosphate?redirect=true>, 2 pages.

Malaysian Office Action in Malaysian Application No. PI 2016000077, dated Jun. 20, 2019, 3 pages.

Australian Office Action in Australian Application No. 2019257368, dated Nov. 5, 2019, 2 pages.

(56) References Cited

OTHER PUBLICATIONS

Brazil Office Action in Brazil Application No. PI 0619817-1, dated Aug. 21, 2019, 16 pages.

Brazilian Office Action in Brazil Application No. BR 112012029653-1, dated Oct. 15, 2019, 5 pages.

Brazilian Office Action in Brazil Application No. BR 112016002671-7, dated Oct. 29, 2019, 5 pages.

Mexican Office Action in Mexican Application No. MX/a/2016/001639, dated Aug. 27, 2019, 7 pages.

Office Action received for Singapore Application No. 10201402492T, dated Oct. 4, 2019, 3 pages.

Peruvian Office Action in Peruvian Application No. 1872.15, dated Aug. 19, 2019, 27 pages.

Philippines Office Action in Philippine Application No. 1/2015/502575, dated Aug. 9, 2019, 3 pages.

Response to Non-Final Office Action dated Oct. 7, 2016, U.S. Appl. No. 14/633,605, 10 pages.

Schwartz et al., "JAK inhibition as a therapeutic strategy for immune and inflammatory diseases," Nat Rev Drug Discov., Dec. 28, 2017, 17(1):78.

Ukrainian Decision to Grant in Ukrainian Application No. a201602100, dated Aug. 30, 2019, 17 pages.

Vietnamese Office Action in Vietnamese Application No. 1-2016-00848, dated Oct. 16, 2019, 4 pages.

Zhao et al., "Inhibition of STAT Pathway Impairs Anti-Hepatitis C Virus Effect of Interferon Alpha," Cell Physiol Biochem. 2016, 40(1-2):77-90.

26th Annual JPMorgan Healthcare Conference presentation dated Jan. 8, 2008, 28 pages.

Abe et al., "Effective Methods for Introducing Some Aryl and Heteroaryl Substituent onto 1-Azaazulene Nuclei", Heterocycles, 2005, 66: 229-240.

Abelson et al., "Alternate reference values for tear film break-up time in normal and dry eye populations, Lacrimal Gland, Tear Film, and Dry Eye Syndromes 3 Part B", Adv Exp Med Biol, 2002,506:1121-1125.

Abelson et al., "Dry eye syndrome: diagnosis, clinical trials, and pharmaceutical treatment-improving clinical trials". Lacrimal Gland, Tear Film, and Dry Eye Syndromes 3 Part B, Adv Exp Med Biol, 2002, 506: 1079-86.

Abstract of Chilean patent application No. 3496-06 published in Official Gazette of the Republic of Chile (Jun. 1, 2007) and publication (2 pages).

Ahmed et al., "Treatment of Pemphigus Vulgaris with Rituximab and Intravenous Immune Globulin," The New England Journal of Medicine, 2006, 1.772-1.779.

Aho et al., Expression of human pim family genes is selectively up-regulated by cytokines promoting T helper type 1, but not T helper type 2, cell differentiation, Immunology, 2005, 116: 82-88.

Albach et al., "Diagnosis of keratoconjunctivitis sicca in rheumatoid arthritis. The value of various tests". Ophthalmologe, Apr. 1994.; 91(2):229-34—in German (with English abstract/summary contained therein).

Anderson et al., "Biochemical characterization of GSK1070916, a potent and selective inhibitor of Aurora B and Aurora C kinases with an extremely long residence time," Biochem J., 2009, 420{2):259-265.

Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.

Arber et al., "The 2046 revision to the World Health. Organization classification of myeloid neoplasms and acute leukemia," Blood, May 2016, 2391-2405.

Argentina Office Action in Argentina Application No., P110100737, dated Mar. 21, 2019, 10 pages.

Argentina Office Action in Argentina Application No. P110101747, dated Jun. 10, 2019, 5 pages.

Argentina Office Action in Argentina Application No. 20120102175, dated Jul. 22, 2019, 10 pages.

Australian Office Action in Australian Application No. 2015222913, dated Jun. 17, 2019, 5 pages.

Australian Office Action, in Australian Application No., 2016204689, dated Mar. 22, 2017, 4 pages.

Bachmann et al., "The serine/threonine kinase Pim-1," The International Journal of Biochemistry and Cell Biology, 2005, 37: 726-730.

Bain et al, "Chronic neutrophilic leukaemia," in: Swerdlow, et al., eds. WHO Classification of Turners of Haematopoietic and Lymphoid Tissues (ed 4th). Lyon: IARC Press, 2008: 38-39.

Banker et al., "Modem Pharmaceuticals" Third Edition, 1996, 596.

Barabino et al., "Tear film and ocular surface tests in animal, models of dry eye; uses and limitations," Experimental Eye Research, 2004, 79: 613-621.

Barr et al., "Corneal scarring in the Collaborative Longitudinal Evaluation of Keratoconus (CLEK) Study: baseline prevalence and repeatability of detection", Cornea, 1999, 18(1);34-46.

Baudouin et al., "Flow cytometry in impression cytology specimens. A new method for evaluation of conjunctival Inflammation," Invest Ophthalmol Vis Set, 1997, 38: 1458-1464.

Baxter et al., "Acquired mutation of the tyrosine kinase JAK2 in human myeloproliferative disorders," Lancet, 2005, 365:1054-1061.

Baxter et at., "Reductive Animations of Carbonyl Compounds with Borohydride and Borane Reducing Agents," Organic Reactions, 2002, 1-57.

Baytel et al., "The human Pim-2 proto-oncogene and its testicular expression," Biochimica et Biophysica Acta, 1998, 1442; 274-285.

Beck et al., "Brief Report: Alleviation of Systemic Manifestations of Castleman's Disease by Monoclonal Anti-interleukin-6 Antibody." *N. Engl J. Med.*, 1994, 330(9):602-605.

Begley et al., "Use of the dry eye questionnaire to measure symptoms of ocular irritation in patients with aqueous tear deficient dry eye", Cornea, 2002, 21: 664-70.

Bell and Zalay, "Synthesis of Substituted 3-Amino[6, 5-b] triazinoindoles." Journal of Heterocyclic Chemistry, Oct. 1975, 12(5): 1001-1004.

Bennett et al., "Proposals for the classification of the myelodysplastic syndromes," British Journal of Haematology, 1982, 51: 189-199.

Berge et al., "Pharmaceutical salts", J. Pharma. Science, 1977, 66(1): 1-19.

Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

Bhattacharya et al., "Polymorphism in Pharmaceutical Solids," Second Edition, 2009, 192:327-345.

Bhovi et al., "1 , 3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-38.

Edward B. Roche, "Bioreversible Carriers in Drug Design," American Pharmaceutical Association and Pergamon Press, 1987, Front Matter, 4 pages.

Blom et al., "Optimizing Preparative LC/MS Configurations and Methods for Parallel Synthesis Purification," J. Comb. Chem., 2003, 5: 670-683.

Blom et al, "Preparative LC-MS Purification: Improved Compound-Specific Method Optimization," J. Comb. Chem., 2004, 6: 874-883.

Blom, "Two-Pump at-Column-Dilution Configuration for Preparative Liquid Chromatography—Mass Spectrometry," J. Comb. Chem., 2002, 4: 295-301.

Blume-Jensen et al., "Oncogenic kinase signaling", Nature, 2001, 411(6835):355-365.

Bock et al., "Managing drug resistance in cancer: lessons from HIV therapy," Nature, Jul. 2012, 12:494-501.

Bolen, "Nonreceptor tyrosine protein kinases", Oncogene, 1993, 8(8):2025-31.

(56) References Cited

OTHER PUBLICATIONS

Bollrath et al., "gp130-Mediated Stat3 Activation in Enterocytes Regulates Cell Survival and Cell-Cycle Progression during Colitis-Associated Tumorigenesis," Cancer Cell, 2009, 15:91-102.
Bondoux et al., "Palladium-catalyzed C—C coupling: efficient preparation of new 5-thio-B-D-xylopyranosides as oral venous antithrombotic drugs," Tetrahedron Letters, 2009, 50(27): 3872-3876.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12): 1756-64.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al., "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brazil Office Action in Brazil Application No. BR11201303270-0, dated Jul. 30, 2019, 5 pages.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," invest Ophthalmol Vis Sci, 2000, 41:1356-1363.
Brignole et al., "Flow cytometric analysis of inflammatory markers in KCS: 6-mouth treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.
Brunning et al., "Myelodysplastic syndromes/neoplasms, overview;" WHO Classification of Tumours of Haematopoietic and Lymphoid Tissues, 4th edition, 2008, 88-103.
Brunton et al., "Chemotherapy of Neoplastic Diseases," Goodman & Gilman's; The Pharmacological Basis of Therapeutics, 11th edition, 2008, 853-908.
Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib, Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.
Canadian Examination Report in Canadian Application No. 2,799,928, dated Nov. 26, 2018, 3 pages.
Canadian Office Action in Canadian Application No. 2,738,520, dated Jul. 16, 2018, 7 pages.
Cancer.org "Breast Cancer," American Cancer Society, [retrieved on Dec. 1, 2014] retrieved from URL <http://7www.cancer.org.cancer/breastcancer/detailedguide/breast-cancer-prevention>, 4 pages.
Candotti et al., "Molecular aspects of primary immuno-deficiencies: lessons from cytokine and other signaling pathways.", J Clin Invest, May 2002, 109(10); 1261-9.
Candotti et al., "Structural and functional basis for JAK3-deficient severe combined immunodeficiency", Blood, 1997, 90(10): 3996-4003.
Carey and Sundberg, Advanced Organic Chemistry, Part B: Reactions and Synthesis, 4th ed., Kluwer Academic/Plenum Publishers: New York, 2001, 111-119.
Carey and Sundberg, Advanced Organic Chemistry, Part B: Reactions and Synthesis, Oxidations, 4th ed., Kluwer Academic/Plenum Publishers: New York, 2001, 747-757.
Cazzola et al., American Society of Hematology (ASH Education Book), 2011(1), 2011, 264-272.
Cermak et al, "Is complete androgen insensitivity syndrome associated with alterations in tire meibomian gland and ocular surface," Cornea, 2003, 22:516-521.
Cervantes et al., "Three-year efficacy, safety, and survival findings from COMFORT-II, a phase 3 study comparing ruxolitinib with best available therapy for mylefibrosis," Blood, Dec. 12, 2013, 122(25):4047-4053.
Cetkovic-Cvrlje et al., "Targeting JAK3 with JANEX-1 for prevention of autoimmune type 1 diabetes in NOD mice", Clin Immunol, 2003, 106(3): 213-25.
Chalandon, "Targeting mutated protein tyrosine kinases and their signaling pathways in hematologic malignancies," Haematologica, 2005, 90(7):949-68.
Chan, "Skin inflammatory disorders," In In Vivo Models of Inflammation, 2006, 85-120.
Changelian et al., "Prevention of Organ Allograft Rejection by a Specific Janus Kinase 3 Inhibitor", Science, 2003, 302: 875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(31:333-337.
Chauhan et al, "Autoimmunity in Dry Eye due to resistance of Th17 to Treg Suppression", J. Immunology, 2009, 182(3):1247-52.
Chauhan et al., "A concise review on sustained drug delivery system and its opportunities," International Journal on Pharmtech Research, Mar. 2012, 2: 227-238.
Chemical encyclopedia publication "Soviet Encyclopedia," Moscow, 1988, 1:242-243.
Chen et al., "Blockade of interleukin-6 signaling augments regulatory T-cell reconstitution and attenuates the severity of graft-versus-host disease," Blood, Jul. 2009, 114(4): 891-900.
Chen et al., "Stat3 Activation in Human Endometrial and Cervical Cancer", British Journal of Cancer, 2007, 96: 591-599.
Chen et al., "Induction of myelodysplasia by myeloid-derived suppressor cells," J Clin Invest, Nov. 2013, 123(11): 4595-611.
Cheson et al., "Report of an international working group to standardize response criteria for myelodysplastic syndromes," Blood, Dec. 2000, 96(12): 3671-4.
Chew et al., "An instrument for quantifying meibomian lipid on the lid margin: the Meibometer", Curr Eye Res, 1993, 12:247-254.
Chew et al., "The casual level of meibomian lipids in humans", Current Eye Research, 1993, 12:255-259.
Chilean Office Action in Chilean Application No. 292-02016, dated Jul. 18, 2019, 5 pages.
Chinese Notice of Reexamination in Chinese Application No. 201080033675.6, dated May 10, 2016, 18 pages (English Translation).
Chinese Office Action in Chinese Application No. 201480024761.9, dated Oct. 8, 2016, 21 pages (English Translation).
Chinese Office Action in Chinese Application No., 201480052299.3, dated Jan. 25, 2018, 13 pages.
Chinese Office Action in Chinese Application No. 201610989522.8, dated Jun. 4, 2018, 19 pages.
Chinese Office Action in Chinese Application No. 2015/0017178.X, dated Jul. 24, 2019, 24 pages.
Chinese Office Action in Chinese Application No. 201580017178, dated Nov. 8, 2018, 10 pages.

(56) References Cited

OTHER PUBLICATIONS

Cho et al., "Review of the (ear break-up time and a closer look at the tear break-up time of Hong Kong Chinese", Optom Vis Sci, 1993, 70(1);30-8.
Choi Ha-Soon et al., "Design and synthesis of 7H-pyrrolo[2,3-d]pyrimidines as focal adhesion kinase inhibitors. Part 1", Bioorg. & Med. Chem. Lett., 2006, 16(8):2173-2176.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002,46(12) 3143-3150.
Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995. 60(17): 5721-5725.
Cilloni et al., "Emerging drugs for chronic myeloid leukemia", Expert Opinion on Emerging Drugs, Jun. 2010, 15(2): 175-184.
Claessens et al., "In vitro proliferation and differentiation of erythyroid progenitors from patients with myelodysplastic syndromes: evidence for Fas-dependent apoptosis," Blood, Mar. 2002, 1594-1601.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al, "Discovery and Development of Janus Kinase (JAK) inhibitors for Inflammatory Diseases," J Med Chem., 2014, A-P.
Clevelandclinic.org, "Lupus," Feb. 2001, [retrieved on Dec. 1 5, 2018] retrieved from URL <https://rny.clevelandclinic.org/health/di8e3ses/4875-lupus>, 7 pages.
Clinical Trial NCT01787487 ('487 Trial), dated Feb. 7, 2013, 6 pages.
ClinicalTrials.gov, <http:clinicaltrials.gov/ct2/show/NCT00227591>, downloaded Dec. 6, 2016.
ClinicalTrials.gov, "Topical Ruxolitinib for the Treatment of Vitiligo," Retrieved on Dec. 19, 2018, retrieved from URL <clinicaltrials.gov/ct2/show/NCT02809976>, 6 pages.
ClinicalTrials.gov, "A Study to Evaluate the Safety and Efficacy of INCB018424 Phosphate Cream Applied Topically to Adults With Atopic Dermatitis," Retrieved on Dec. 19, 2018, retrieved from URL <https://ciinicaltrials.gov/ct2/show/NCT03011892>, 7 pages.
Winyard, P.G. and Willoughby, D.A., "Inflammation, Protocols," Humana Press, Methods in Molecular Biology: 2003, vol. 225, 359 pages.
Colombian Office Action in Colombian Application No. 12-213. 010, dated Jun. 17, 2014, 20 pages.
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Costa Rican Office Action in Costa Rican Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al., "Tear lipid layer structure and stability following expression of the meibomian glands", Ophthalmic Physiol Opt, 1995, 15(6):569-74.
Coligan, "Current Protocols in Immunology," Wiley Press, 1988, vol. 3, Chapter abstracts only, 21 pages.
Daniels et al., "Imatinib mesylate inhibits the profibrogenic activity of TGF-? and prevents bleomycinmediated lung fibrosis," J. Clin. Invest., Nov. 2004, 114(9): 1308-1316.
Danjo et al., "Observation of precorneal tear film in patients with Sjogren's syndrome", Acta Ophthalmol Scand, 1995, 73:503-505.
De Paiva et al., "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells", Br J Haematol, 2000, 109(4): 823-8.
Deng Jun et al., "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Divkovic et al., "Hapten-protein binding; from theory to practical application in the in vitro prediction of skin sensitization," Contact Dermatitis, 2005, 189-200.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1,2,4]triazino[1,6-c]quinazolin-5-ium-1-olates," Tetrahedron, 1974, 30:3997-4012.
Dorwald, "Side Reactions in Organic Synthesis; A Guide to Successful Synthesis Design," Wiley-VCH, 2005, Chapter 1, 32 pages.
Dudley et al., "A VEGF/JAK2/STAT5 axis may partially mediate endothelial cell tolerance to hypoxia", Biochem. J., 2005, 390(Pt 2):427-36.
Methods in Molecular Biology: vol. 225, Inflammation Protocols., Winyard, P.G. and Willoughby, D.A., Humana Press, 2003 Duplicate Reference.
Ecuador Examination Report in Ecuador Application No. SP-12-12546, dated Mar. 29, 2019, 12 pages.
Eghtedar et al., "Phase 2 study of the JAK kinase inhibitor ruxolitinib in patients with refractory leukemias, including postmyeloproliferative neoplasm acute myeloid leukemia," Blood, May 2012, 119(20): 4614-4618.
Eghtedar, "Phase 11 Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Elliott et al., "WHO-defined chronic neutrophilic leukemia: a long-term analysis of 12 cases and a critical review of the literature," Leukemia, 2005, 19:313-317.
Eurasian Office Action in Eurasian Application No. 201291310, dated Mar. 9, 2017, 4 pages (English Translation).
Eurasian Search Report in Eurasian Application No. 201200132, dated Sep. 1, 2016, 6 pages (English Translation).
Eurasian Office Action in Eurasian Application No. 201691745, dated Mar. 20, 2019, 4 pages.
European Communication in European Application No. 06839328.5, dated Jan. 22, 2009, 5 pages.
European Communication pursuant to Article 94(3) EPC in European Application No. 14753182.6, dated Nov. 6, 2017, 10 pages.
European Communication pursuant to Article 94(3) EPC in European Application No. 14753182.6, dated Sep. 10, 2018, 7 pages.
European Office Action in European Application No., 15195698.4, dated Mar. 15, 2017, 4 pages.
European Search Report in European Application No. 16197502.4, dated Mar. 20, 2017, 15 pages.
European Extended Search Report in European Application No. 18191992.9, dated Jan. 18, 2019,10 pages.
European Opposition in European Application No. 16197502.4, dated Jul. 18, 2019, 22 pages.
Expert Scientific Group on Phase One Clinical Trials Final Report, Nov. 30, 2006, pp. C1, C35-C38.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.

(56)          References Cited

OTHER PUBLICATIONS

Fayad et al., "Interleukin-6 and interleukin-10 levels in chronic lymphocytic leukemia: correlation with phenotypic characteristics and outcome," Blood, Jan. 2001, 97(1): 256-263.

Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.

Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.

Fiskus et al, "Synergistic Activity of Combinations of JAK2 Kinase Inhibitor with P13K/mTOR, MEK or PIM Kinase Inhibitor Against Human Myeloproliferative Neoplasm Cells Expressing JAK2V617F", J. American Chem. Soc., 52nd Annual Meeting of the American-Society-of-Hematology (ASH); Orlando, FL, USA; Dec. 4-7, 2010, ACS Publications; vol. 116, No. 21, Nov. 1, 2010 p. 349, XP002667216, ISSN: 0002-7863 (1 page).

Fleischman et al., "The CSF3R T618I mutation causes a lethal neutrophilic neoplasia in mice that is responsive to therapeutic JAK inhibition," Blood, Nov. 2013, 122: 3628-3632.

Flex et al., "Somatically acquired JAK1 mutations in adult acute lymphoblastic leukemia", J. Exp Med., 2008, 205:751-8.

Fonseca et al., "Interleukin-6 as a key player in systemic inflammation and joint destruction", Autoimmunity Reviews, 2009, 8:538-42.

Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.

Foucar, "Myelodysplastic/Myeloproliferative Neoplasms," Am J Olin Pathol, 2009, 132:281-289.

Fridman et al., "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).

Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).

Fridman et al, "Discovery and Preclinical Development of Selective JAK inhibitors for the Treatment of Hematological Malignancies" poster presented at European Hematology Association, 12th Congress, Vienna, Austria. Abstract: 0324, Jun. 8, 2007 (3 page).

Fridman et al., "Discovery and Preclinical Development of Selective JAK Inhibitors for the Treatment, of Myeloproliferative Disorders" poster presented at the 4th International Congress on Myeloproliferative Diseases and Myelodysplastic Syndromes, New York, NY. Nov. 8-10, 2007. Poster 0009 (1 page).

Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).

Fridman et al., "Preclinical evaluation of local JAK1 and JAK2 inhibition in cutaneous inflammation", Journal of Investigative Dermatology, Sep. 2011, 131(9): 1838-1844.

Froberg et al., "Demonstration of clonality in neutrophils using FISH in a case of chronic neutrophilic leukemia," Leukemia, 1998, 12:623-626.

Fujihara et al., "Evaluation of human conjunctival epithelium by a combination of brush cytology and flow cytometry: an approach to the quantitative technique", Diagn Cytopathol, 1997, 17:456-60.

Fujii et al., "Aberrant expression of serine/threonine kinase Pim-3 in hepatocellular carcinoma development and its role in the proliferation of human hepatoma cell lines" International Journal of Cancer, 2005, 114: 209-218.

Fukagawa et al., "Histological evaluation of brush cytology of rabbit conjunctiva", Nippon Ganka Gakkai Zasshi, 1993, 97:1173-8 (contains English abstract within the article).

Furqan et al., "Dysregulation of JAK-STAT pathway in hematological malignancies and JAK inhibitors for clinical application," Biomarker Research 2013, 1(1): 1-10.

Gaertner, "Cyclization of 1-Alkylamino-3-halo-2-alkanols to 1-Alkyl-3-azetidinols," J. Org. Chem., 1967, 32:2972-76.

Gaestel et al., "Targeting innate immunity protein kinase signalling in inflammation," Nat Rev Drug Discov., Jun. 2009, 8(6):480-99.

Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.

Gilchrist et al., "5H-2-Pyrindines from 2-Bromocyclopentene-1-carboxaldehyde," Tetrahedron, Jan. 1, 1995, 9119-9126.

Glasson et al., "Differences in clinical parameters and tear film of tolerant and intolerant contact lens wearers," Invest Ophthalmol Vis Sci, 2003, 44:5116-5124.

Glattfeld, "Improvements in the Preparation of DL-Threonic and DL-Erythronic Acids", J. Am. Chem. Soc., 1940, 62:974-977.

Gobbels et al., "Tear secretion in dry eyes as assessed by objective fiuorophotometry," Ger J Ophthalmol, 1992, 1:350-353.

Golding et al., "X-ray and scanning electron, microscopic analysis of the structural composition of tear fans", Cornea, Jan. 1994, 13(1):58-66.

Gomtsyan et al., "Design, synthesis, and structure-activity relationship of 6-alkynylpyrimidines as potent adenosine kinase inhibitors," J. Med. Chem., 2002, 45(17):3639-3648.

Goodman et al., "IL-6 Signaling in Psoriasis Prevents Immune Suppression by Regulatory T Cells," J. Immunol., Sep. 2009, 183: 3170-3176.

Gooseman et al., "The intramolecular b-fluorine . . . ammonium interaction in 4- and 8-membered rings", Chem. Commun, 2006, 30:3190-3192.

Gorre et al., "Clinical Resistance to STI-571 Cancer Therapy Caused by BCR-ABL Gene Mutation or Amplification." Science, 2001, 293:876-880.

Gotlieb, Alice, Presentation at the 2008 American Academy of Dermatology, 66th Annual Meeting, San Antonio, TX, Feb. 1, 2008, symposium-303 (12 pp.).

Goto et al., "Color mapping of tear lipid layer thickness distribution from the image analysis in DR-1 tear lipid layer interference images," ARVO abstract, 2004, 2 pages.

Goto et al., "Computer-synthesis of an interference color chart of human tear lipid layer by a colorimetric approach," Invest Ophthalmol Vis Sci, 2003, 44:4693-7.

Goto et al., "Differentiation of lipid tear deficiency dry eye by kinetic analysis of tear interference images," Arch Ophthalmol, 2003, 121:173-80.

Goto et al., "Evaluation of the tear film stability after laser in situ keratomileusis using the tear film stability analysis system," Am J Ophthalmol, Jan. 2004, 137(1):116-20.

Goto et al., "Kinetic analysis of tear interference images in aqueous tear deficiency dry eye before and after punctal occlusion," Invest Ophthalmol Vis Sci, 2003, 44:1897-905.

Goto et al., "Tear Film Stability Analysis System: introducing a new application for videokeratography", Cornea, Nov. 2004, 23(8):S65-S70.

Gottlieb, "Psoriasis: Emerging Therapeutic Strategies," Nat Rev Drug Disc., Jan. 2005,4:19-34.

Grabbe et al., "Immunoregulatory mechanisms involved in elicitation of allergic—contact hypersensitivity," Immunol Today, Jan. 1998, 19(1):37-44 (only 1 page provide and marked "best available").

Green and Wuts, P.G.M., Protective Groups in Organic Synthesis, 3rd. Ed., Wiley & Sons, Inc., New York (1999).

Greenberg, "The Role of Hemopoietic Growth Factors in the Treatment of Myelodysplastic Syndromes," International Journal of Pediatric Hematology/Oncology, 1997, 4(3); 231-238.

Greenberg, "The myelodysplastic syndromes" in Hoffman, et al., eds. Hematology: Basic Principles and Practice (3rd ed.), Churchill Livingston; 2000; 1106-1129.

(56) References Cited

OTHER PUBLICATIONS

Greene et al., Greene's Protective Groups in Organic Synthesis, 2007, 4th Edition, 54-55.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, "Tear film photography and contact lens wear", J Br Contact Lens Assoc, 1982;5:84-7.
Gura, "Systems for identifying New Drugs Are Often Faulty." Science. Nov. 1997, 278(5340):1041-1042.
Gurram et al., "C—C Cross-Coupling Reactions of)6-Alkyl-2-Haloinosine Derivatives and a One-Pot Cross-Coupling/)6-Deprotection Procedure," Chem Asian J., Aug. 2012, 7(8): 1853-1861.
Guschin et al., "A major role for the protein tyrosine kinase JAK1 in the JAK/STAT signal transduction pathway in response to interleukin-6", Embo J 14:1421-1429 (1995).
Hamzé et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Harris et al., "World Health Organization classification of neoplastic diseases of the hematopoietic and lymphoid tissues: report of the Clinical Advisory Committee meeting—Airlie House. Virginia, Nov. 1997," J Clin Oncol 1999, 17:3835-3849.
Heine et al., "The JAK-inhibitor ruxolitinib impairs dendritic cell function in vitro and in vivo," Blood, 2013, 122(7):1192-1202.
Helal et al., "Stereoselective Synthesis of cis-1,3-Disubstituted Cyclobutyl Kinase Inhibitors," Organic Letters, (2004), 6(11), pp. 1853-1856.
Hengge et al., "Adverse Effects of Topical Glucocorticosteroids," J Am Acad Dermatol., Jan. 2006, 54(1):1-15.
Hernandez et al., "Clinical, hematological and cytogenetic characteristics of atypical chronic myeloid leukemia," Ann. Oncol, Apr. 2000, 11(4): 441-444.
Hickenbottom, "Reactions of organic compounds," State Scientific-Technical Publishing Association, Chemical Literature Section, Moscow, 1939, pp. 360-362.
Higuchi et al., "Pro-drugs as Novel Delivery Systems," vol. 14 of the A.C.S. Symposium Series (1975).
Holly et al., "Lacrimation kinetics in Humans as determined by a novel technique", in Holly FJ (ed). The preocular tear film, Lubbock TX, Lubbock Dry Eye Institute, 1986, pp. 76-88.
Hong et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Hungarian Office Action in Hungarian Application No. S1700017/5, dated Aug. 28, 2018, 5 pages.
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," *Transplantation*, 2010, 90(8):825-835.
Indian Office Action in Indian Application No. 2177/DELNP/2014, dated May 8, 2018, 4 pages.
Indonesian Office Action in Indonesian Application No. P00201605769, dated May 13, 2019, 6 pages.
Indonesian Office Action in Indonesian Application No. P00201506279, dated Jul. 11, 2019, 5 pages.
International Preliminary Report on Patentability (with Written Opinion) dated Nov. 22, 2013 for International Appln. No. PCT/US2010/035728, 8 pages.
International Preliminary Report on Patentability (with Written Opinion) dated Nov. 22, 2011 for International Appln. No. PCT/US2010/035783, 5 pages.
International Preliminary Report on Patentability (with Written Opinion) in International Application No. PCT/US2006/047369, dated Jun. 18, 2008, 10 pages.
International Preliminary Report on Patentability (with Written Opinion) in International Application No. PCT/US2010/047252, dated Mar. 6, 2012, 7 pages.
International Preliminary Report on Patentability for International Appln. No. PCT/US2008/066662 dated Dec. 17, 2009, 7 pages.
International Preliminary Report on Patentability for PCT/US2008/66658 mailed Dec. 17, 2009, 7 pages.
International Preliminary Report on Patentability for PCT/US2009/036635 mailed Sep. 14, 2010, 6 pages.
International Preliminary Report on Patentability for PCT/US2009/059203 mailed Apr. 5, 2011, 6 pages.
International Preliminary Report on Patentability tor PCT/US2010/021003 mailed Jul. 19, 2011, 11 pages.
International Preliminary Report on Patentability for PCT/US2010/052011 mailed Apr. 11, 2012, 4 pages.
International Preliminary Report on Patentability for PCT/US2011/025433 mailed Aug. 21, 2012, 7 pages.
International Preliminary Report on Patentability for PCT/US2011/027665 mailed Sep. 11, 2012, 7 pages.
International Preliminary Report on Patentability for PCT/US2011/037291 mailed Nov. 27, 2012, 7 pages.
International Preliminary Report on Patentability for PCT/US2011/061351 mailed May 30, 2013, 7 pages.
International Preliminary Report on Patentability for PCT/US2011/061374 mailed May 30, 2013, 5 pages.
International 'Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Preliminary Report on Patentability for PCT/US2013/041601, issued Nov. 18, 2014, 7 pages.
International Preliminary Report on Patentability in International Application No. PCT/US2014/049940, dated Feb. 9, 2016, 9 pages.
International Preliminary Report on Patentability in International Application No. PCT/US2014/051678, dated Mar. 3, 2016, 15 pages.
International Preliminary Report on Patentability in international Application No. PCT/US2015/028224, dated Nov. 10, 2016, 7 pages.
International Search Report and the Written Opinion, PCT/US2012/051439, mailed Nov. 30, 2012, 15 pages.
International Search Report and the Written Opinion, PCT/US2012/053921, mailed Nov. 7, 2012, 19 pages.
International Search Report and Written Opinion dated Feb. 9, 2010 for International Appln. No. PCT/US2009/059203, 10 pages.
International Search Report and Written Opinion for International Appln. No. PCT/US2005/046207 dated May 15, 2007, 6 pages.
International Search Report and Written Opinion for International Appln. No. PCT/US2008/066662 dated Dec. 23, 2008, 11 pages.

(56) References Cited

OTHER PUBLICATIONS

International Search Report and Written Opinion for International Appln. No. PCT/US2009/036635 dated Jun. 3, 2009, 14 pages.
International Search Report and Written Opinion for PCT/US2006/047369, 16 pages (Apr. 24, 2007).
International Search Report: and Written Opinion for PCT/US2008/083319, 29 pages mailed Mar. 13, 2009.
International Search Report and Written Opinion for PCT/US2011/025433, 12 pages (mailed Jul. 20, 2011).
International Search Report and Written Opinion for PCT/US2011/027665 mailed Jun. 27, 2011, 14 pages.
International Search Report and Written Opinion for PCT/US2011/037291, 11 pages (Apr. 19, 2012).
International Search Report and Written Opinion for PCT/US2011/061351 mailed Feb. 17, 2012, 12 pages.
International Search Report and Written Opinion for PCT/US2011/061374 mailed Mar. 27, 2012, 12 pages.
International Search Report and Written Opinion for PCT/US2012/025581, 16 pages (mailed Apr. 26, 2012).
International Search Report and Written Opinion for PCT/US2012/043099, 11 pages (Sep. 13, 2012).
International Search Report: and Written Opinion for PCT/US2012/050252 mailed Jan. 2, 2013, 17 pages.
International Search Report and Written Opinion in International Application No. PCT/US2013/067794, mailed Dec. 17, 2013, 14 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No., PCT/US2014/051678, dated Feb. 11, 2015, 22 pages.
International Search Report and Written Opinion in International Application. No. PCT/US2015/017963, dated Jun. 5, 2015, 13 pages.
International Search Report and Written Opinion in International Application No. PCT/US2015/028224, dated Jul. 21, 2015, 9 pages.
International Search Report and Written. Opinion in International Application No. PCT/US2015/033254, dated Oct. 7, 2015, 12 pages.
International Search Report for PCT/US2008/66658 mailed Dec. 23, 2008, 4 pages.
International Search Report for PCT/US2010/021003 mailed Aug. 16, 2010, 8 pages.
International Search Report for PCT/US2010/035728 mailed Jul. 8, 2010, 3 pages.
International Search Report for PCT/US2010/035783 mailed Aug. 23, 2010, 4 pages.
International Search Report for PCT/US2010/047252 mailed Nov. 17, 2010, 4 pages.
International Search Report for PCT/US2010/052011 mailed Nov. 30, 2010, 3 pages.
International Search Report in International Application No. PCT/US2013/041601, mailed Sep. 3, 2013, 3 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al., "Expedient Synthesis of Potent Cannabinoid Receptor Agonist (−)-CP55,940", Organic Letters, 2005, 7(19): 4181-4183.
Jädersten et al., "Long-term outcome of treatment of anemia in MDS with erythropoietin and G-CSF," Blood, Aug. 2005, 106(3): 803-11.
James et al., "A unique clonal JAK2 mutation leading to constitutive signalling causes polycythaemia vera", Nature, 434 (7037): 1144-8 (2005).
Janes et al., Effective and selective targeting of leukemia cells using a TORC1/2 kinase inhibitor Nature Medicine (2010) LNKD-PUBMED:20072130, vol. 16, No. 2, pp. 205-213 XP002673719.
Japanese Office Action in Japanese Application No. 2013-540049, dated Aug. 11, 2015, 3 pages (English Translation).
Japanese Office Action in Japanese Application No. 2015-042933, dated Feb. 2, 2016, 6 pages (English Translation).
Japanese Office Action in Japanese Application No. 2015-219637, dated Oct. 4, 2016, 6 pages.
Japanese Office Action in Japanese Application No. 2015-241393, dated Sep. 27, 2016, 5 pages (English Translation).
Japanese Office Action in Japanese Application No. 2015-561582, dated Feb. 13, 2018, 9 pages (English Translation.).
Japanese Office Action in Japanese Application No. 2016-143513, dated May 23, 2017,3 pages (English Summary).
Japanese Office Action in Japanese Application No. 2017-000685, dated Jan. 31, 2017, 7 pages (with English translation).
Japanese Office Action in Japanese Application No. 2017-246-134, dated Oct. 16, 2018, 12 pages.
Japanese Office Action in Japanese Application No. 2016-554471, Nov. 27, 2018, 8 pages.
Japanese Office Action in Japanese Application No. 2018-070780, Jul. 2, 2019, 5 pages.
Jee et al., "Overview: animal models of osteopenia and osteoporosis", J Musculoskel. Neuron, Interact., 2001, 1(3):193-207.
Jester et al., "In vivo biomicroscopy and photography of meibomian glands in a rabbit model of meibomian gland dysfunction", Invest Ophthalmol Vis Sci, 1982, 22:660-7.
Johnson et al., "The effect of instilled fluorescein solution volume on the values and repeatability of TBUT measurements", Cornea, 2005, 24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syndromes", Graefe's Arch Clin Exp Ophthalmol, 2004, 495-500.
Kamb, "What's wrong with our cancer models?", Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., Abstract #1956, "A Phase 2, Randomized, Dose-Ranging, Vehicle-and Active-Controlled Study to Evaluate the Safety and Efficacy of Ruxolitinib Cream in Adult Patients with Atopic Dermatitis," Presentation, Presented at the 27th European Academy of Dermatology and Venereology Congress, Sep. 12-16, 2018, Paris, France, 11 pages.
Kim et al., "Clinical significances of preoperative serum interleukin-6 and C-reactive protein level in operable gastric cancer," BMC Cancer, May 20, 2009, 9(155):1-9.
Kim et al., "Zinc-Modified Cyanoborohydride as a Selective Reducing Agent," J. Org. Chem., 1985, 50: 1927-1932.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.

(56) References Cited

OTHER PUBLICATIONS

Kojima et al., "A new noninvasive tear stability analysis system for the assessment of dry eyes", Invest Ophthalmol Vis Sci, 2004, 45(5): 1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Kontzias et al., "Jakinibs: a new class of kinase inhibitors in cancer and autoimmune disease," Curr. Opin. Pharm., 2012, 12: 464-470.
Korb et al., "Increase in tear film lipid layer thickness following treatment of meibomian gland dysfunction", Adv Exp Med Biol, 1994, 350:293-8.
Korb et al., "The effect of two novel lubricant eye drops on tear film lipid layer thickness in subjects with dry eye symptoms", Optom Vis Sci, 2005, 82: 594-601.
Korean Office Action in Korean Application No., 10-2018-7025131, dated Oct. 31, 2018, 7 pages (English Translation Only).
Korean Office Action in Korean Application No. 10-2012-7033308, dated Mar. 21, 2017, 6 pages (English Translation Only).
Korolev et al., "Pd-EDTA as an efficient catalyst for Suzuki-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kruh et al., "The complete coding sequence of arg defines the Abelson subfamily of cytoplasmic tyrosine kinases.", Proc. Natl. Acad. Sci., Aug. 1990, 87:5802-5806.
Kubinyi, "QSAR: Rausch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24):2305-23.
Kuo et al., "Pd-EDTA as an efficient catalyst for Suzuki-Miyaura reactions in water", Chem Commun, 2007, 301-303.
Kuppens et al., "Basal tear turnover and topical timolol in glaucoma patients and healthy controls by Fluorophotometry", Invest Ophthalmol Vis Sci, 1992, 33:3442-3448.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase 1, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kuster, "Kinase Inhibitors," Methods and Protocols, 2012, 46 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al., "Tear Cytokine Profiles in Dysfunctional Tear Syndrome", Am J Ophthalmol., 2009, 147(2): 198-205.
Larock, "Comprehensive Organic Transformations", Wiley-VCH, 2nd Ed, (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitinib," Leukemia, 2014, 3 pages.
Leaf, "Why are we losing the war on cancer (and how to win it)," Clifton, Health Administrator vol. XVII, 2005, 1:172-183.
Lemp, "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye Workshop", The Ocular Surface, 5(2), 75-92 Apr. 2007.
Letter translation of Office Action, Chilean Application No. 3496-2006 as received from the foreign associate (Jul. 5, 2010) (4 pages).
Levine et al., "Activating mutation in the tyrosine kinase JAK2 in polycythemia vera essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Li et ah, "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Li et al., "The synthesis and the antitumor activity of 5,7-disubstituted pyrazolo [1,5-a] pyrimidines," Chinese 3 Med Chem., Feb. 28, 2007, 17(1):18-22.
Liesveld and Lichtman, Chapter 88. "Myelodysplastic Syndromes (Clonal Cytopenias and Oligoblastic Myelogenous Leukemia)", in Prchal et al., eds. Williams Hematology. 8th ed., New York: McGraw-Hill; 2010.
Lima and Barreiro, "Bioisosterism: a useful strategy for molecular modification and drug design," Curr Med Chem., 2005,12(1):23-49.
Lin et al., "Enantioselective synthesis of Janus kinase inhibitor INCB018424 via an organocatalytic aza-Michael reaction," Organic Letters, 2009, 11(9): 1999-2002.
Lin, "Constitutive Activation of JAK3/STAT3 in Colon Carcinoma Tumors and Cell Lines," Am J Pathol., 2005, 167(4):969-80.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22); 6891-6900.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2):349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdCl2 in Aqueous Acetonitrile", Organic Letters, 2005, 7(23): 5237-39.
Main et al., "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Malaysian Examination Report in Malaysian Application No. PI2013002970, dated May 31, 2016,4 pages.

(56) References Cited

OTHER PUBLICATIONS

Mancini et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.

Mandal, "Cancer Classification," 2014. Available from: <http://www.news-medical.net/health/Cancer-Classification.aspx, 6 pages.

Manjula et al., "Rapid Method of Converting Primary Amides to Nitrites and Nitrites to Primary Amides by ZnCl2 using Microwaves under Different Reaction Conditions", Syn. Common, 2007, 37:1545-50.

Manning et al., "The Protein Kinase Complement of the Human Genome," Science, 2002, 298(5600): 1912-16 and 1933-34.

Mao et al., "Advances in research of tyrosine kinases inhibitor of vascular endothelial growth factor receptor," Chinese J New Drugs, Dec. 31, 2008, 17(7):544-550.

March, Jerry, Advanced Organic Chemistry: Reactions, Mechanisms, and Structure, 3rd ed., John Wiley & Sons:New York, pp. 845-855 (1985).

Marelli et al., "Tumor targeting via integral ligands," Frontiers in Oncology, Jan. 12, 2013.

Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.

Maruyama et al., "Effect of environmental conditions on tear dynamics in soft contact lens wearers," Invest Ophthalmol Vis Sci, 2004, 45(8):2563-8.

Mascarenhas et al., "Ruxolitinib: The First FDA Approved Therapy for the Treatment of Myelofibrosis," Clinical Cancer Research, Jun. 2012, 18(11): 3008-3014.

Matano et al., "Deletion of the long arm of chromosome 20 in a patient with chronic neutrophilic leukemia: cytogenetic findings in chronic neutrophilic leukemia," Am. T. Hematol., Jan. 1997, 54(1): 72-5.

Mathers et al., "Assessment of the tear film with tandem scanning confocal microscopy", Cornea, 1997; 16:162-8.

Mathers et al., "Tear film changes associated with normal aging", Cornea, 1996; 15:229-334.

Mathers et al., "Tear flow and evaporation in patients with and without dry eye", Ophthalmology, 1996, 103:664-669.

Mathers et al., "Video imaging of the meibomian gland", Arch Ophthalmol, 1994, 112:448-9.

Mathers, "Evaporation from die ocular surface", Exp Eye Res, 2004, 78:389-394.

Maxson et al., "Oncogenic CSF3R Mutations in Chronic Neutrophilic Leukemia and Atypical CML," *N. Engl. J. Med.*, 2013, 368091:1781-1790.

MayoClinic.org, "Heart Transplant," 2018, [retrieved Dec. 8, 2018] retrieved from URL <https://www.mayoclinic.org/tests-procedures/heart-transplant/about/pac-20384750>, 18 pages.

Mayo Clinic. Available at: <http://www.mayoclinic.com/health/pancreatic-cancer/DS00357 >. 2 pages, retrieved from the Internet Apr. 3, 2013.

Mayo Clinic, Available at: < http://www.mayoclinic.com/health/prostate-cancer-prevention/MC00027 >. 3 pages, retrieved from the Internet Apr. 3, 2013.

Mayo Clinic. Available at: <http://www.mayoclinic.com/health/crohns-disease/DS00104/DSECTION=treatments-and-drugs> 6 pages, retrieved from the Internet May 27, 2013.

Mayo Clinic. Available at: <http://www.mayoclinic.com/health/multiple-sclerosis/DS00188/DSECTION=treatments-and-drugs>. 3 pages, retrieved from the Internet May 27, 2013.

Mayo Clinic. Available at: <http://www.mayoclinic.com/health/myasthenia-gravis/DS0037S> 2 pages, retrieved from the Internet May 27, 2013.

Mayo Clinic. Available at: <http://www.mayoclinic.com/health/rheumatoid-arthritis/DS00020/DSECTION=treatments-and-drugs> 3 pages, retrieved from the Internet Jun. 26, 2013.

Mayo Clinic. Available at: <http//www.mayoclinic.org/diseases-conditions/type-1-diabetes/basics/prevention> 2014, 19 pages.

McMillan, "The systemic inflammation-based Glasgow Prognostic Score: a decade of experience in patients with cancer," Cancer Treat Rev, Aug. 2013, 39(5): 534-40.

McNamara et al., "Fluorometry in contact lens research: The next step," Optom Vis Sci, 1998, 75:316-322.

MD Anderson Cancer Center, "Leukemia Prevention and Screening," 2014, 2 pages.

MD Anderson Cancer Center, "Myeloproliferative Disease Prevention and Screening," 2014, 2 pages.

Mengher et al., "Non-invasive tear film break-up time: sensitivity and specificity", Acta Ophthalmol (Copenh), 1986, 64(4):441-4.

Mesa et al., "INCB018424, A Selective JAK 1/2 Inhibitor, Significantly Improves the Compromised Nutritional Status and Frank Cachexia in Patients with Myelofibrosis (MR)" Poster #1760 at the American Society of Hematology Annual Meeting (ASH), Dec. 6, 2008 (19 pages).

Mesa et al., "Emerging drugs for the therapy of primary and post essential thrombocythemia, post polycythemia vera myelofibrosis", Expert Opinion on Emerging Drugs England, 2009, 14(3): 471-479.

Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.

Mexican Office Action in Mexican Application No. MX/a/2016/001639, Jun. 7, 2019, 2 pages.

Meydan et al., "Inhibition of acute lymphoblastic leukaemia by a Jak-2 inhibitor", Nature, Feb. 1996, 379(6566): 645-8.

Meyer et al., "Anti-inflammatory activity and neutrophil reductions mediated by the JAK1/JAK3 inhibitor, CP-690,550, in rat: adjuvant-induced arthritis," Journal of Inflammation, Jan. 12, 2010.

Miethchen, "Micelle-activated reactions. 1. Micelle-activated iodination and partial dehalogenation of pyrazoles and 1,2,4-triazoles", Journal F. prakt. Chemie. Band 331, Heft 5, S. 799-805 (1989) (1 page abstract also provided).

Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi et al., "Human Tyrosine Kinase 2 Deficiency Reveals Its Requisite Roles in Multiple Cytokine Signals Involved in Innate and Acquired Immunity", Immunity, 2006, 25:745-55.

Mishchenko et al., "Treatment options for hydroxyurea-refractory disease complications in myeloproliferative neoplasms; JAK2 inhibitors, radiotherapy, splenectomy and transjugular intrahepatic portosystemic shunt", Eur J Haematol., Sep. 2010, 85(3); 192-9 Epub Jun. 2, 2010.

Mishima et al., "Determination of tear vol. and tear flow", Invest Ophthalmol, 1966, 5:264-276.

Mishima, "Some physiological aspects of the precorneal tear film", Arch Ophthalmol, 3965, 73:233-241.

Mitsunobu, "The Use of Diethyl Azodicarboxylate and Triphenylphosphine in Synthesis and Transformation of Natural Products." Synthesis, 1981, (1): 1-28.

Miyata el al., "Stereospecific nucleophilic addition reactions to olefins", J. Org. Chem., 1991, 56:6556-6564.

Miyaura et al., "Palladium-Catalyzed Cross-Coupling Reactions of Organoboron Compounds," Chem. Rev., 1995, 95: 2457-2483.

Miyoshi et al., "Interleukin-8 concentrations in conjunctival epithelium brush cytology samples correlate with neutrophil, eosinophil infiltration, and corneal damage", Cornea, 2001, 20:743-7.

Molldrem et al., "Antithymocyte globulin for patients with myelodysplastic syndrome," Br J Haematol, Dec. 1997, 99(3): 699-705.

Moreland et al., "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.

(56) References Cited

OTHER PUBLICATIONS

Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al., "JAK mutations in high-risk childhood acute lymphoblastic leukemia", Proc Natl Acad Sci USA, 2009, 106:9414-8.
Mundle et al., "Evidence for Involvement of Tumor Necrosis Factor-a in Apoptotic Death of Bone Marrow Cells in Myelodysplastic Syndromes," Am J Hematol, 1999, 60:36-47.
Naka, "The paradigm of IL-6: from basic science to medicine", Arthritis Res., 2002, 4 Suppl 3:S233-42.
Nakagawara, "Trk receptor tyrosine kinases: A bridge between cancer and neural development," Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Namour et al., "Once-daily High Dose Regimens of GLPG0634 in Healthy Volunteers are Safe and Provide Continuous Inhibition of JAK1 but not JAK2," ACR/ARHP Annual Meeting 12, Nov. 9-14, 2012, Abstract No. 1331.
Naqvi et al., "A potential role of ruxolitinib in leukemia", Expert Opinion on Investigational Drugs, Aug. 2011, 20(8): 11.59-1166.
National Cancer Institute, "Cancer Types by Site," Mar. 14, 2011, [retrieved from Dec. 15, 2018] retrieved from URL <https:/web.archive.org/web/20110314030905/https://training.seer.cancer.gov/disease/categories/site.html>, 3 pages.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Navigatingcancer.com, "List of Cancer Chemotherapy Drugs," Navigating Care, [retrieved on Nov. 26, 2013] retrieved from URL <https://www.navigatingcancer.com/library/all/chemotherapy drugs>, 6 pages.
Neidle, Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Neuner et al., "Increased IL-6 Production by Monocytes and Keratinocytes in Patients with Psoriasis," J. Invest. Dermatol., 1991, 97: 27-33.
Nicholoff et al., "Recent Insights into the immunopathogenesis of psoriasis provide new therapeutic opportunities", J. Clin, Invest, 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishimoto et, al., "Improvement in Castleman's disease by humanized anti-interleukin-6 receptor antibody therapy," *Blood*, 2000, 95(1):56-61.
Nishio et al., "Tyrosine kinase-dependent modulation by interferon-a of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," Expert Opinion, Informa Healthcare, 2012, available at: <http://informahealthcare.com/dol/pdfplus/10.1517/13543776.2012.723693>.
Norn, "Quantitative tear ferning. Clinical investigations", Acta Ophthalmol (Copenh), 1994, 72(3):369-72.
Notice of Allowance and Fee(s) Due dated Sep. 21, 2007 in connection with U.S. Appl. No. 11/313,394, 6 pages.
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702, 9 pages.
Office Action (Non-final) dated Dec. 3, 2007 in connection with U.S. Appl. No. 11/524,641, 13 pages.
Office Action (Non-final) dated Feb. 25, 2009 for U.S. Appl. No. 12/137,892, 13 pages.
Office Action (Final) dated Feb. 7, 2008 for U.S. Appl. No. 11/115,702, 5 pages.
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394, 16 pages.
Office Action in U.S. Appl. No. 14/186,338, mailed May 5, 2014,18 pages.
Office Action received for European Application No. 06 839 328.9 (Jan. 22, 2009), 5 pages.
Office Action received for Japanese Application No. 2008-545733 dated Oct. 11, 2011 (5 pages).
Office Action received for New Zealand Application No. 569015 dated Feb. 24, 2010, 2 pages.
Office Action Received for New Zealand Application No. 748000, dated Dec. 24, 2018, 2 pages.
Office Action received for New Zealand Application No. 749437, dated Jul. 8, 2019, 2 pages.
Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012, 3 pages.
Office Action, China. Patent Application No. 201080033308.6 dated Aug. 2, 2013, 10 pages.
Office Action, Eurasian Patens Office Application No. 200870048, prepared Feb. 5, 2010.
Office Action, European Patent Office, Application No. 06 839 328.9 mailed Oct. 21, 2010.
Office Action, European Patent: Office, mailed Nov. 6, 2009 Application 06839328.9.
Office Action, Mexico, Patent Appl. No. MX/a/2008/007635 as received from foreign associate dated Jun. 15, 2010, 1 page.
Office Action, Mexico, Patent Appl. No. MX/a/2008/007635 as received from foreign associate dated Nov. 13, 2009, 4 pages.
Office Action/Examination Report received for Pakistan Application No. 211/2009 dated Jan. 18, 2010, 1 page.
Oguz et al., "The height and radius of the tear meniscus and methods for examining these parameters", Cornea, 2000, 19:497-500.
Opposition for EP Patent 1966202, filed on Jun. 21, 2012, 30 pages.
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008, 6 pages (English Translation).
Ortmann et al., "Janus kinases and signal transducers and activators of transcription: their roles in cytokine signaling, development and immunoregulation," Arthritis Res, 2000, 2(1): 16-32.
O'shea et al., "Janus Kinase Inhibitors in Autoimmune Diseases," Ann Theum Dis., Apr. 2013, 72(Suppl 2):ii1 1 1-ii115.
Osteoporosis.aaos.org[online], "Osteoporosis," Feb. 2001, [retrieved on Dec. 15, 2018] retrieved from URL <https://orthoinfo.aaos.org/en/diseases--conditions/osteoporosis/>, 7 pages.

(56) References Cited

OTHER PUBLICATIONS

Ostojic et al., "Ruxolitinib: a new JAK1/2 inhibitor that offers promising options for treatment of myelofibrosis," Future Oncology, 2011, 7(9): 10354043.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Panteli et al., "Serum interleukin. (IL)-1, IL-2, sIL-2Ra, IL-6 and thrombopoietin levels in patients with chronic myeloproliferative diseases," British Journal of Haematology, 2005, 130: 709-715.
Pardanani et al., "CSF3R T618I is a highly prevalent and specific mutation in chronic neutrophilic leukemia," Leukemia, 2013, 27: 1870-1873.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach toTreating Rheomatoi.html>, 12 pages.
Patani et al., "Bioisosterism: A Rational Approach in Drug Design", Chem. Rev., 1996, 96: 3147-3176.
Patel et al., "Formulation and Evaluation of Controlled Release Matrix Tablet of a Model Antibiotic Drug," Am, J. Pharm Tech. Res., 2012 2(2).
Patrick, "An Introduction to medicinal chemistry" *Oxford University Press Inc.*, New York. 1995 (31 pages) (cited in Opposition from India dated Nov. 12, 2012.
Pearce et al., "An improved fluorophotometric method for tear turnover assessment", Optom Vis Sci, 2001, 78(1):30-36.
Pearce et al., "Spatial location studies on the chemical composition of human tear ferns", Ophthalmic Physiol Opt, 2000, 20(4):306-13.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Pensyl et al., "The repeatability of tear mucus ferning grading", Optom Vis Sci, 1998, 75(8):600-4.
Pernis et al., JAK-STAT signaling in asthma. Clin Invest, 2002, 109(10): 1279-83.
Peters et al., "Functional Significance of Tie2 Signaling in the Adult Vasculature", 2004, © The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Philippines Examination Report in Philippines Application No. 1-2013-501001, dated Mar. 23, 2017, 3 pages.
Philippines Notice of Allowance in Philippines Application No. 1/2015502575, Jun. 27, 2019, 3 pages.
Philippines Office Action in Philippines Application No. 1/2016/500243, Jun. 25, 2019, 4 pages.
Pillonel, "Evaluation of phenylaminopyrimidines as antifungal protein kinase inhibitors," Pest Management Science, Wiley & Sons, Jun. 2005, 61: 1069-1076.
Picard et al., "Classification of Kinase Inhibitors Using BCUT Descriptors", J. Chem. Inf. Comput. Sci., 2000, 40:1431-1440.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Pisella et al., "Flow cytometric analysis of conjunctival epithelium in ocular rosacea and keratoconjunctivitis sicca," Ophthalmology, 2000, 107:1841-1849.
Portnaya et, al., "Azomethine dyes, IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Prchal et al., "Williams Hematology," New York: McGraw-Hill, 2010, 8th ed., Front Matter, 7 pages.
Press Release dated Sep. 18, 2008: "Incyte's Topical JAK Inhibitor Demonstrates Positive Proof-of-Concept Results in Patients with Mild to Moderate Psoriasis" (4 pages).
Press Release dated Sep. 13, 2018: "Incyte Announces Positive Data from Phase 2b Trial of Ruxolitinib Cream in Patients with Atopic Dermatitis" (2 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Product Monograph, "Jakavi," Prepared Jun. 15, 2012, Last revised, Sep. 28, 2018, 51 pages.
PubChem CID: 222786, "Cortisone," retrieved on Mar. 6, 2019, retrieved from URL<https://pubchem.ncbi.nih.gov/compound/cortisone#section=Chemical-and-Physical-Properties>, 39 pages.
PubChem CID: 5865, "Prednisone," retrieved on Mar. 6, 2019, retrieved from URL<https://pubchem.ncbi.nlm.nih.gov/compound/prednisone#section=Top>, 90 pages.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis," Journal of the American Academy of Dermatology. vol. 60, No. 3, 360 Park Avenue South, New York, NY 10030-1710 USA; Mosby-Elsevier, 2009.
Quesada et al., "One-pot conversion, of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAKI/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115( 15):3109-3117.
Raoof et al., "12-Week Efficacy and Safety Data of Ruxolitinib Cream in Adult Patients with Atopic Dermatitis: Results from a Phase 2 Study," Presented at die 24th World Congress of Dermatology, Milan, Italy, Jun. 10-15, 2019, 15 pages.
Ravin, "Preformulation", Remington's Pharmaceutical Sciences, 17th ed., Mack Publishing Company, Easton, Pa., 1985, Chapter 76, 1409-1423.
Raza et al, "Novel insights into the biology of myelodyplastic syndromes; excessive apoptosis and the role of cytokines," Int J Hematol, 1996, 63:265-278.
Raza et al, "The Myelodysplastic Syndromes in 1996: Complex Stem Cell Disorders Confounded by Dual Action s of Cytokines," Leak Res, 1996, 20:881-890.
Raza et al., "Apoptosis in bone marrow biopsy samples involving stromal and hematopoietic cells in 50 patients with myelodysplastic syndromes," Blood, Jul. 1995, 86(1): 268*76.
Raza et al, "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Ren el al, "Compounds and Compositions as Protein Kinase inhibitors," U.S. Appl. No. 60/578,491, filed Jun. 10, 2004 (56 pages).

(56) References Cited

OTHER PUBLICATIONS

Response and Amendment dated Aug. 25, 2009 to non-final Office Action for U.S. Appl. No. 12/137,892, 34 pages.
Response and Amendment in Reply to Action of Apr. 20, 2007 filed Jul. 17, 2007 for U.S. Appl. No. 11/313,394, 39 pages.
Response to Action of Aug. 22, 2007 dated Nov. 19, 2007, U.S. Appl. No. 11/115,702, 7 pages.
Response to Restriction Requirement dated May 29, 2007, U.S. Appl. No. 11/115,702, 8 pages.
Restriction Requirement dated Mar. 6, 2007 in connection with U.S. Appl. No. 11/115,702, 8 pages.
Reuters, "Jakafi (ruxolitinib) improved advanced pancreas cancer outcomes in mid-stage trial" Internet Citation, Aug. 21, 2013, pp. 1-2, XP002717211, Retrieved from Internet: URL: http://www.curetoday.com/index.cftn/foseaction/news,showNewsArticle/id/l3/news_id/3785 [retrieved on Nov. 29, 2013].
Riese et.: al, "Inhibition of JAK kinases in patients with rheumatoid arthritis: scientific rationale and clinical outcomes," Best Practice & Research Clinical Rheumatology, 2010, 513-526.
Roberts et al., "Trends in the Risks and Benefits to Patients With Cancer Participating in Phase 1 Clinical Trials," JAMA, 2004, 292(17):2130-2140.
Robin et al, "In vivo transillumination biomicroscopy and photography of meibomian gland dysfunction," Ophthalmology, 1985, 92:1423-6.
Rodig et al., "Disruption of the Jak1 gene demonstrates obligatory and nonredundant roles of the Jaks in cytokine-induced biologic responses." Cell, 1998, 93(3); 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear, 1st Intern Tear Film Symposium. Lubbock (Texas, USA), Dry Eye Institute, 1986,203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001,45{Supplement 2): S203-S210.
Rolando, "Tear mucus ferning test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model", Agents Actions, 1993, 38(1-2): 116-21.
Rousvoal et al., "Janus kinase 3 inhibition with CP-690,550 prevents allograft vasculopathy", Transpl Int., 2006, 19(12): 1014-21.
Roy et al., "Formulation and design of sustained release matrix tablets of metformin hydrochloride: Influence of hypromellose and polyacrylate polymers," Int J Appl Basic Med Res., Jan. 2013, 3(I):55-63.
Saemann et al., "Suppression of early T-cell-receptor-triggered cellular activation by the Janus kinase 3 inhibitor MHI-P-154," Transplantation, 2003, 75(11): 1864-1872.
Saemann et al, "Prevention of CD40-triggered dendritic cell maturation and induction of T-cell hyporeactivity by targeting of Janus kinase 3," Am J Transplant, 2003, 3(11): 1341-9.
Saettone and Salminen, "Ocular inserts for topical delivery", Advanced Drug Delivery Reviews, 1995, 16:95-106.
Samanta et al., "Janus kinase 2: a critical target in chronic myelogenous leukemia," Cancer Res., Jul. 2006, 66(13):6468-72.
Santini et al., Hepcidin Levels and Their Determinants in Different Types of Myelodysplastic Syndromes/PLoS One, 2011, 6(8): e23109, pp. 1-8.
Sawada et al., "Increased Lipophilicity and Subsequent Cell Partitioning Decrease Passive Transcellular Diffusionof Novel, Highly Lipophilic Antioxidants", The Journal of Pharmacology and Experimental Therapeutics, 1999, 288(3): 1317-1326, p. 1321, compound 26.
Schiffer, "Clinical issues in the management of patients with myelodysplasia" Hematology Am Soc Hematol Educ Program, 2006, 205-10.
Schiffer, "Myelodysplasia: the good, the fair and the ugly," Best Pratt Res Clin Haematol, Mar. 2007, 20(1): 49-55.
Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007. 352-356.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Scott et al., "Prolonged responses in patients with MDS and CMML treated with azacytidine and etanercept," (British Journal of Haematology), Mar. 2010, 148(6): 944-947.
Search Report in TW Application No. 100117866, dated Dec. 2014, 1 page.
Seefeld et al., "Discovery of 5-pyrrolopyridinyl-2-thiophenecarboxaimdes as potent AKT kinase," Bioorganic & Medicinal Chemistry Letters, 2009, 19(8):2244-2248.
Seela et al., "Synthesis of Pyrrolo[2,3-d]pyrimidine 2',3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol, 2004, 24(4):931-4.
Seto et al., "Enhanced Th2 cell-mediated allergic inflammation in Tyk2-deficient mice," J Immunol, 2003, 170(2): 1077-83.
Shah et al., "Multiple BCR-ABL kinase domain mutations confer polyclonal resistance to the tyrosine kinaseinhibitor imatinib (ST1571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol May 2008, 26(15): 2505-11.
Smith et al., "Basic pathogenic mechanisms operating in experimental model acute anterior uveitis," Immunology and Cell Biology, 1998, 76: 497-512.
Smolen et al., "Effect of interleukin-6 receptor inhibition with tocilizumab in patients with rheumatoid arthritis (Option study): a double-blind, placebo-controlled, randomized trial". Lancet, 2008, 371:987.
Sonbol et al., "Comprehensive review of JAK inhibitors in myeloproliferative neoplasms," Therapeutic Advances in Hematology, 2013, 4(1): 15-35.
Song et al., "JAK1 Activates STAT3 Activity in Non-Small-Cell Lung Cancer cells and IL-6 Neutralizing Antibodies can Suppress JAKI-STAT3 Signaling," Mol Cancer Ther., Mar. 2011, 10(3): 481-94.
Spoerl et al., "Activity of therapeutic JAK 1/2 blockade in graft-versus-host disease," Blood, 2014, 123(24): 3832-3842.
Srdan et al., "Safety and Efficacy of INCB018424, a JAK 1 and JAK2 inhibitor, in Myelfibrosis," The New England Journal of Medicine, Sep. 16, 2010,363:1117-1127.

(56) References Cited

OTHER PUBLICATIONS

Sri Lanka Office Action in Sri Lanka Application No. 18621, May 16, 2019, 1 page.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol, Chem., 2004,279(19): 19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
Stahl et al., "Topical Administration," Handbook of Pharmaceutical Salts, 22(43): 110.
State Intellectual Property Office, PR China, Office Action, dated Sep. 3, 2010 Pat. Appl. No. 200680052750,7 (8 +A601+A597.
Steensma et al., "The JAK2 V617F activating tyrosine kinase mutation is an infrequent event in both "atypical" myeloproliferative disorders and mylodysplastic syndromes," Blood, Aug. 2005,106(4): 1207-9.
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., "The relationship of serum IL-6 levels to acute graft-versus-host disease and hepatorenal disease after human bone marrow transplantation," Transplantation, 1992, 54(3): 457-462 (Abstract only).
Taiwanese Office Action in Taiwanese Application. No. 103126987, dated Dec. 28, 2017, 9 pages (English Translation).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sei USA, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1, 1995: 1353-3358.
Tan. et al., "Racemization processes at a quaternary carbon center in the context of the asymmetric Michael reaction", Tetrahedron Lett., 2001,42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al., "The Clinical Phenotype of Myelofibrosis Encompasses a Chronic Inflammatory State that isFavorably Altered by INCB018424, A Selective Inhibitor of JAK1/2" Poster #2804 at the American Society of Hematology Annual Meeting (ASH), Dec. 7, 2008, (18 pages).
Tefferi et al., "Serious adverse events during ruxolitinib treatment discontinuation in. patients with myelofibrosis", Mayo Clinic Proceedings, Dec. 2011, 86(12): 1188-1191.
Tefferi, "Primary myelofibrosis: 2012 update on diagnosis, risk stratification, and management," American Journal of Hematology, Dec. 2011, 86(12): 1017-1026.
Textbook of Clinical Trials 264 (D. Machin et al., eds., 2nd eds., 2006).
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract), Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer". Cancer Lett, 2003, 201(1): 107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol 1990, 34(2):233-5.
Tsubota et al., "Detection by brush cytology of mast cells and eosinophils in allergic and vernal conjunctivitis," Cornea, 1991, 10(6):525-31.
UCSFheaUh.org, "Liver Cancer," UCSF Medical Center, [retrieved on Nov. 9, 2018], retrieved from URL <https://www.ucsfhealth.org/conditions/liver_cancer/<, 3 pages.
Ueda et al., "1,2-Benzisoxazol-3-yl Diphenyl Phosphate: A New, Reactive Activating Agent for the Synthesis of Amides, Esters, and Peptides via Condensation", J. Org, Chem., 1985, 50:760-763.
Vaillant et al., "Turbidity of pulpy fruit juice: A key factor for predicting cross-flow microfiltration performance," J Membrane Sci., 2008, 325:404-412.
Van Best et al., "Measurement of basal tear turnover using a standardized protocol", Graefe's Arch Clin Exp Ophthalmol, 1995, 233:1-7.
Van Bijsterveld, "Diagnostic tests in the sicca syndrome", Arch Ophthalmol, 1969, 82:10-14.
Van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64,10: S1051-1.
Vannucchi et al., "Inhibitors of P13K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vannucchi et al., "The mTOR Inhibitor, RAD001, Inhibits the Growth of Cells From Patients with Myeloproliferative Neoplasms", Blood: ASH Annual Meeting Abstracts, 51st Annual Meeting of the American Society of Hematology, 2009, 114(22), 2 pages.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press; 2008:80-81.
Vardiman et al., "The 2008 revision of the World Health Organization (WHO) Classification of myeloid neoplasms and acute leukemia: rationale and important changes," Blood, 2009, 114:937-951.

(56)                References Cited

OTHER PUBLICATIONS

Vardiman et al., "The World Health Organization (WHO) classification of the myeloid neoplasms," Blood, 2002, 100:2292-2302.

Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.

Venugopal et al., "Special clinical concerns/problems in the management of MDS and secondary acute myeloid leukemias," Cancer Treat Res, 2001, 108: 257-65.

Verma et al., "Jak family of kinases in cancer", Cancer and Metastasis Reviews, 2003, 22(4): 423-434, DOI: 10.1023/A:1023805715476.

Verstovsek, "Therapeutic Potential of JAK2 Inhibitors", Hematology Am Soc Hematol Educ Program, 2009:636-42.

Verstovsek, et al., Blood (ASH Annual Meeting Abstracts) 2007 110: Abstract 558.

Verstovsek, et al., Blood (ASH Annual Meeting Abstracts) 2009 114: Abstract 311.

Verstovsek, et al., Blood (ASH Annual Meeting Abstracts) 2010 116: Abstract 313.

Verstovsek, S. et al., "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).

Verstovsek, S. et al., "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

Verstovsek, S. et al., INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of Jaks V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).

Verstovsek et al., "Efficacy, safety and survival with ruxolitinib in patients with mylefibrosis:results of a median 2-year follow-up of COMFORT-1," Haematologica, 2013, 98(12):1865-1871.

Vietnamese Office Action in Vietnamese Application No. 1-2011-02964, dated Jun. 26, 2019, 2 pages.

Vietnamese Office Action in Vietnamese Application No. 1-2019-03042, dated Jun. 21, 2019, 2 pages.

Vietnamese Office Action in Vietnamese Application No. 1-2015-03693, dated Jun. 4, 2019, 2 pages.

Vietnamese Office Action in Vietnamese Application No. 1-2014-00977, dated Jul. 22, 2019, 2 pages.

Vitali et al., "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.

Wagh et al., "Polymers used in ocular dosage form and drug delivery systems", Asian J. Pharm., Jan. 2008, 12-17.

Wang and Deisboeck, "Mathematical modeling in cancer drug discovery," Drug Discovery Today, 2014, 145-150.

WebMD, "Diabetes Health Center," Available at: < http://diabetes, webmd.com/guide/diabetestreatment_care>. 3 pages, retrieved from the Internet May 28, 2013.

Webster's New World Medical Dictionary, Sjogren's syndrome, 2003, Wiley Publishing, printed from http://www.eredoreference.com/entry/webstermed/sjogren_s_syndrome, 2 pages.

Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.

Welch et al., "An approach to a more standardized method of evaluating tear film break-up lime", Invest Ophthalmol Vis Sci, 2003, 2485/B324 (abstract only—2 pages).

White et al., Human basic tear fluid osmolality. I. Importance of sample collection strategy, Acta Ophthalmol (Copenh), Aug. 1993, 71(4):524-9.

Wilks, "The JAK kinases: Not just another kinase drug discovery target," Seminars in Cell & Developmental Biology, 2008, 319-328.

Williams and Ibrahim, "Carbodiimide Chemistry: Recent Advances", Chem. Rev., 1981, 81:589-636.

Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.

Williams, et al., "Initial Efficacy of INCB018424, a selective Janus Kinase 1& 2 (JAK1&2) Inhibitor in RheumatoidArthritis (RA)," European League Against Rheumatism (EULAR) meeting presentation and abstract (Jun. 11-14, 2008, Paris, France). Annals Rheum Dis 67SII:62, 2008.

Winfield, Pharmaceutical Practice, Ophthalmic Products—pH adjustment, Churchill Livingstone, 2004,264-271.

Wolff et al., "Burger's Medicinal Chemistry and Drug Discovery", 5th Ed Part 1, 1995, 975-977.

Wu et al., One-Pot Two-Step Microwave-Assisted Reaction in Construction 4,5-Disubstituted Pyrazolopyrimidines Organic Letters, 2003, 5(20): 3587-3590.

Wuts and Greene, Protective Groups in Organic Synthesis, 4th ed., John Wiley & Sons: New Jersey, (2007).

Xiong, "Inhibition of JAK 1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.

Yamamura et al., "Circulating interleukin-6 levels are elevated in adult T-cell leukaemia/lymphoma patients and correlate with adverse clinical features and survival," Br. J. Haematol., 1998, 100: 129-134.

Yamaoka et al., "Janus kinase (JAK) inhibitors in rheumatoid arthritis", Current Rheumatology Reviews, Nov. 2011, 7(4): 306-312.

Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.

Yao et al., "Glucocorticoid-Induced Bone Loss in Mice Can Be Reversed by the Actions of Parathyroid Hormoneand Risedronate on Different Pathways for Bone Formation and Mineralization", Arthritis and Rheumatism, 2008, 58(11):3485-3497.

Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.

Yokoi et al., "A newly developed video-meibography system featuring a newly designed probe", Jpn J Ophthalmol, 2007, 51: 53-6.

Yokoi et al., "Assessment of meibomian gland function in dry eye using meibometry", Arch Ophthalmol, 1999, 117:723-9.

Yokoi et al., "Correlation of tear lipid layer interference patterns with the diagnosis and severity of dry eye", Am J Ophthalmol, 1996, 122:818-24.

Yokoi et al., "Non-invasive methods of assessing the tear film", Exp Eye Res, 2004, 78:399-407.

Younes et al., "Phase 1 Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.

Yu et al., "Role of Janus Kinase/Signal Transducers and Activators of Transcription in the Pathogenesis of Pancreatitis and Pancreatic Cancer," Gut and Liver, Oct. 2012, 6(4): 417-422.

(56) References Cited

OTHER PUBLICATIONS

Yu et al., "Constitutive activation of the Janus kinase-STAT pathway in T lymphoma overexpressing the Lck protein tyrosine kinase," J Immunol., 1997, 159(11):5206-10.
Zaidi et al., "Dermatology in Clinical Practice," Springer, 2010, 157 pages.
Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al., "Signaling Pathways Activated by Oncogenic Forms of Abl Tyrosine Kinase." Journal of Biological Chemistry, 1999, 274(26): 18141-18144.
Pre-Grant Opposition filed on Apr. 8, 2022 Against Indian Patent Application No. 10745/DELNP/2012 (Cover Letter, Index, Opposition).
Annexure 1—Claims, to Opposition filed on Apr. 8, 2022 Against Indian Patent Application No. 10745/DELNP/2012.
Annexure 2 to Opposition filed on Apr. 8, 2022 Against Indian Patent Application No. 10745/DELNP/2012; Incyte'sTopical JAK Inhibitor Demonstrates Positive Proof-of-Concept Results in Patients with Mild to Moderate Psoriasis, Sep. 18, 2008.
Annexure 5 to Opposition filed on Apr. 8, 2022 Against Indian Patent Application No. 10745/DELNP/2012; Stern, "Psoriasis," The Lancet, vol. 350, pp. 349-353, Aug. 2, 1997.
Annexure 6 to Opposition filed on Apr. 8, 2022 Against Indian Patent Application No. 10745/DELNP/2012; Bronaugh et al,, "Topical Absorption of Dermatological Products," Marcel Dekker, Inc.
Representation for Opposition to Grant of Patent, filed in Opposition filed on Apr. 8, 2022 Against Indian Patent Application No. 10745/DELNP/2012.
Argentina Office Action in Argentina Application No. P110101747, dated Aug. 7, 2020, No Translation.
Rowe et al., "Handbook of Pharmaceutical Excipients," Pharmaceutical Excipients, 2006, 5:503-511, 821-823.

(a)

(b)

(b)

(a)

(b)

(a)

(a) (b)

(b)

(a)

TOPICAL FORMULATION FOR A JAK INHIBITOR

This is a continuation of U.S. Ser. No. 17/541,439, filed Dec. 3, 2021, which is U.S. Ser. No. 16/948,408, filed Sep. 17, 2020, now U.S. Pat. No. 11,219,624, issued on Jan. 11, 2022, which is a continuation of U.S. Ser. No. 16/947,735, filed Aug. 14, 2020, now U.S. Pat. No. 10,869,870, issued on Dec. 22, 2020, which is a divisional of U.S. Ser. No. 16/566,625, filed Sep. 10, 2019, now U.S. Pat. No. 10,758, 543, issued on Sep. 1, 2020, which is a continuation application of U.S. Ser. No. 14/714,820, filed May 18, 2015, now abandoned, which is a continuation of U.S. Ser. No. 13/112, 370, filed May 20, 2011, now abandoned, which claims the benefit and priority of U.S. Provisional Application 61/347, 132, filed May 21, 2010, each of which is incorporated herein by reference in its entirety.

TECHNICAL FIELD

This invention relates to pharmaceutical formulations for topical skin application comprising (R)-3-cyclopentyl-3-[4-(7H-pyrrolo[2,3-d]pyrimidin-4-yl)-1H-pyrazol-1-yl]propanenitrile, or a pharmaceutically acceptable salt thereof, and use in the treatment of skin disorders.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1(Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1):16-32).

Deficiencies in expression of JAKs are associated with many disease states. For example, Jak1-/- mice are runted at birth, fail to nurse, and die perinatally (Rodig, S. J., M. A. Meraz, et al. (1998) (*Cell* 93(3): 373-83). Jak2-/- mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract.

Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.,* 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins −2, −4, −6, −7, −12, −15, −18, and −23 as well as GM-CSF and IFNg, signal through the Janus (JAK) kinases (*Adv Pharmacol.* 2000;47:113-74). As such, blocking signal transduction at the level of JAK kinases may result in therapeutic benefits in patients suffering from psoriasis or other immune disorders of the skin.

Given the usefulness of JAK inhibitors in the treatment of skin disorders, there is a need for improved topical formulations of JAK inhibitors. In particular, there is a need for stable, easily applied formulations for JAK inhibitors with good skin permeation characteristics. The formulations of the invention, as well the methods described herein are directed toward this need and other ends.

SUMMARY

A potent JAK1/JAK2 inhibitor, (R)-3-(4-(7H-pyrrolo[2,3-d]pyrimidin-4-yl)-1H-pyrazol-1-yl)-3-cyclopentylpropanenitrile, and its pharmaceutically acceptable salts, has previously been described in U.S. Pat. No. 7,598,257, U.S. Patent Publ. No. 2009/0181959, and U.S. Patent Publ. No. 2008/0312259, each of which is incorporated herein by reference in its entirety. The present invention describes an oil-in-water formulation of (R)-3-(4-(7H-pyrrolo[2,3-d]pyrimidin-4-yl)-1H-pyrazol-1-yl)-3-cyclopentylpropanenitrile suitable for topical administration and treatment of skin disorders.

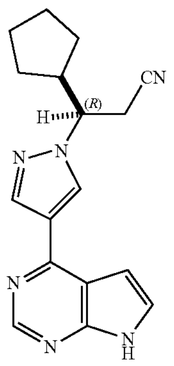

Accordingly, the present invention provides, inter alia, a pharmaceutical formulation for topical skin application, comprising:

an oil-in-water emulsion; and a therapeutically effective amount of a therapeutic agent which is (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

The present invention also provides a method of treating a skin disorder, comprising applying a pharmaceutical formulation described herein to an area of skin of the patient.

The present invention also provides a pharmaceutical formulation described herein for use in treatment of a skin disorder in a patient in need thereof.

The present invention also provides use of a pharmaceutical formulation described herein for the preparation of a medicament for use in treatment of a skin disorder in a patient in need thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
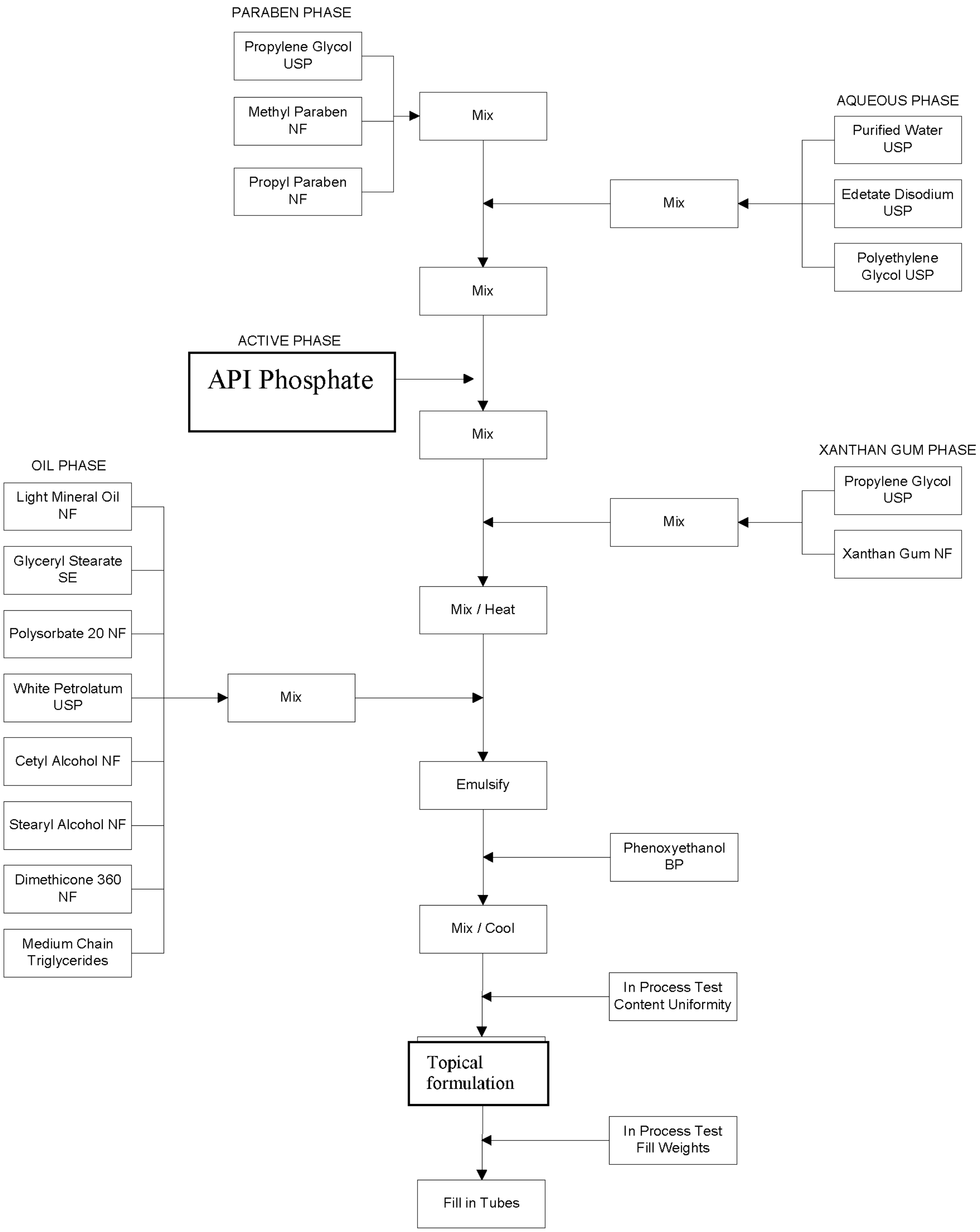
FIG. 1 depicts a flowchart describing the manufacturing process for an oil-in-water formulation of (R)-3-(4-(7H-pyrrolo[2,3-d]pyrimidin-4-yl)-1H-pyrazol-1-yl)-3-cyclopentylpropanenitrile phosphoric acid salt.

Accordingly, the present invention provides, inter alia, a pharmaceutical formulation for topical skin application, comprising a therapeutically effective amount of (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

In some embodiments, the pharmaceutical formulation comprises:

an oil-in-water emulsion; and a therapeutically effective amount of a therapeutic agent which is (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

In some embodiments, the emulsion comprises water, an oil component, and an emulsifier component.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

The oil-in-water formulations were found to have better appearance, spreadability and stability as compared with other formulations. The formulations have a thick, creamy appearance which allows for good spreadability of the formulation on skin. This good spreadability leads to better skin permeation than comparable anhydrous formulations. For example, the oil-in-water formulations showed higher cumulative amounts in studies of transport across human cadaver skin over 24 hours when compared with an anhydrous ointment. While not wishing to be bound by any particular theory, the higher cumulative amounts are believed to be due to better spreadability of the oil-in-water formulation as compared to the anhydrous ointment, resulting in increased surface area for transport. A higher viscosity for the oil-in-water formulations also appeared to be preferred with respect to skin permeation as higher viscosity cream formulations had better transport across human cadaver skin as compared with oil-in-water lotions of lower viscosity.

The oil-in-water formulations described herein were found to have good stability over a three-month period when stored at 25° C./60% RH and 40° C./75% RH in aluminum tubes and maintain reasonable viscosity over time. By comparison, the water-in-oil formulations displayed syneresis when stored at 40° C. (syneresis means separation of liquid from the emulsion).

The water-in-oil formulation was also less desirable than the formulations of the invention, because the API dissolved in the base over time, leading to highly variable skin permeation in in vitro studies as well as a lack of an increase in permeability with increasing strength of the formulation.

In transport studies with freshly excised mouse skin, the oil-in-water formulations also displayed a general trend of increased permeability when the strength of the solubilized cream was increased from 0.5% w/w to 1.5% w/w, while such a trend was not seen with the water-in-oil formulations. Thus, it appears that the water-in-oil emulsions will not have any advantage in terms of providing enhanced permeation with increasing strengths.

Further, the formulations described herein are relatively simple to manufacture with a repeatable process of formulation. The resultant product is easily packaged. The formulations appear to have good stability and relatively consistent permeation profiles.

In some embodiments, the oil component is present in an amount of about 10% to about 40% by weight of the formulation.

In some embodiments, the oil component is present in an amount of about 17% to about 27% by weight of the formulation.

In some embodiments, the oil component is present in an amount of about 20% to about 27% by weight of the formulation.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the formulation.

In some embodiments, the occlusive agent component is present in an amount of about 5% to about 10% by weight of the formulation.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the oil component comprises a stiffening agent component.

In some embodiments, the stiffening agent component is present in an amount of about 2% to about 8% by weight of the formulation.

In some embodiments, the stiffening agent component is present in an amount of about 3% to about 6% by weight of the formulation.

In some embodiments, the stiffening agent component is present in an amount of about 4% to about 7% by weight of the formulation.

As used herein, the term "stiffening agent component" refers to a substance or mixture of substances that increases the viscosity and/or consistency of the formulation or improves the rheology of the formulation.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the oil component comprises an emollient component.

In some embodiments, the emollient component is present in an amount of about 5% to about 15% by weight of the formulation.

In some embodiments, the emollient component is present in an amount of about 7% to about 13% by weight of the formulation.

As used herein, the term "emollient component" refers to an agent that softens or soothes the skin or soothes an irritated internal surface.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the emollient component comprises one or more substances independently selected from light mineral oil, medium chain triglycerides, and dimethicone.

In some embodiments, the water is present in an amount of about 35% to about 65% by weight of the formulation.

In some embodiments, the water is present in an amount of about 40% to about 60% by weight of the formulation.

In some embodiments, the water is present in an amount of about 45% to about 55% by weight of the formulation.

In some embodiments, the emulsifier component is present in an amount of about 1% to about 9% by weight of the formulation.

In some embodiments, the emulsifier component is present in an amount of about 2% to about 6% by weight of the formulation.

In some embodiments, the emulsifier component is present in an amount of about 3% to about 5% by weight of the formulation.

In some embodiments, the emulsifier component is present in an amount of about 4% to about 7% by weight of the formulation.

In some embodiments, the pharmaceutical formulation comprises an emulsifier component and a stiffening agent component, wherein the combined amount of emulsifier component and stiffening agent component is at least about 8% by weight of the formulation.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the pharmaceutical formulation further comprises a stabilizing agent component.

In some embodiments, the stabilizing agent component is present in an amount of about 0.05% to about 5% by weight of the formulation.

In some embodiments, the stabilizing agent component is present in an amount of about 0.1% to about 2% by weight of the formulation.

In some embodiments, the stabilizing agent component is present in an amount of about 0.3 to about 0.5% by weight of the formulation.

As used herein, the term "stabilizing agent component" refers to a substance or mixture of substances that improves the stability of the pharmaceutical formulation and/or the compatibility of the components in the formulation. In some embodiments, the stabilizing agent component prevents agglomeration of the emulsion and stabilizes the droplets in the oil-in-water emulsion.

In some embodiments, the stabilizing agent component comprises one or more substances independently selected from polysaccharides.

In some embodiments, the stabilizing agent component comprises xanthan gum.

In some embodiments, the pharmaceutical formulation further comprises a solvent component.

In some embodiments, the solvent component is present in an amount of about 10% to about 35% by weight of the formulation.

In some embodiments, the solvent component is present in an amount of about 15% to about 30% by weight of the formulation.

In some embodiments, the solvent component is present in an amount of about 20% to about 25% by weight of the formulation.

As used herein, the term "solvent component" is a liquid substance or mixture of liquid substances capable of dissolving (R)-3-(4-(7H-pyrrolo[2,3-d]pyrimidin-4-yl)-1H-pyrazol-1-yl)-3-cyclopentylpropanenitrile or other substances in the formulation. In some embodiments, the solvent component is a liquid substance or mixture of liquid substances in which (R)-3-(4-(7H-pyrrolo[2,3-d]pyrimidin-4-yl)-1H-pyrazol-1-yl)-3-cyclopentylpropanenitrile, or its pharmaceutically acceptable salt, has reasonable solubility. For example, solubilities of (R)-3-(4-(7H-pyrrolo[2,3-d]pyrimidin-4-yl)-1H-pyrazol-1-yl)-3-cyclopentylpropanenitrile (free base) or its phosphate salt are reported in Table 21. In some embodiments, a solvent is a substance or mixture thereof, in which (R)-3-(4-(7H-pyrrolo[2,3-d]pyrimidin-4-yl)-1H-pyrazol-1-yl)-3-cyclopentylpropanenitrile, or its pharmaceutically acceptable salt (whichever is used), has a solubility of at least about 10 mg/mL or greater, at least about 15 mg/mL or greater, or at least about 20 mg/mL or greater, when measured as described in Example 4.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the therapeutic agent is present in an amount of about 0.5% to about 1.5% by weight of the formulation on a free base basis.

In some embodiments, the therapeutic agent is present in an amount of about 0.5% by weight of the formulation on a free base basis.

In some embodiments, the therapeutic agent is present in an amount of about 1% by weight of the formulation on a free base basis.

In some embodiments, the therapeutic agent is present in an amount of about 1.5% by weight of the formulation on a free base basis.

In some embodiments, the therapeutic agent is (R)-3-cyclopentyl-3-[4-(7H-pyrrolo[2,3-d]pyrimidin-4-yl)-1H-pyrazol-1-yl]propanenitrile phosphate.

In some embodiments, the pharmaceutical formulation comprises:

from about 35% to about 65% of water by weight of the formulation;

from about 10% to about 40% of an oil component by weight of the formulation;

from about 1% to about 9% of an emulsifier component by weight of the formulation;

from about 10% to about 35% of a solvent component by weight of the formulation;

from about 0.05% to about 5% of a stabilizing agent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 40% to about 60% of water by weight of the formulation;

from about 15% to about 30% of an oil component by weight of the formulation;

from about 2% to about 6% of an emulsifier component by weight of the formulation;

from about 15% to about 30% of a solvent component by weight of the formulation;

from about 0.1% to about 2% of a stabilizing agent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 17% to about 27% of an oil component by weight of the formulation;

from about 3% to about 5% of an emulsifier component by weight of the formulation;

from about 20% to about 25% of a solvent component by weight of the formulation;

from about 0.3% to about 0.5% of a stabilizing agent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 17% to about 27% of an oil component by weight of the formulation;

from about 4% to about 7% of an emulsifier component by weight of the formulation;

from about 20% to about 25% of a solvent component by weight of the formulation;

from about 0.3% to about 0.5% of a stabilizing agent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments:

the oil component comprises one or more substances independently selected from petrolatums, fatty alcohols, mineral oils, triglycerides, and dimethicones;

the emulsifier component comprises one or more substances independently selected from glyceryl fatty esters and sorbitan fatty esters;

the solvent component comprises one or more substances independently selected from alkylene glycols and polyalkylene glycols; and the stabilizing agent component comprises one or more substances independently selected from polysaccharides.

In some embodiments:

the oil component comprises one or more substances independently selected from white petrolatum, cetyl alcohol, stearyl alcohol, light mineral oil, medium chain triglycerides, and dimethicone;

the emulsifier component comprises one or more substances independently selected from glyceryl stearate and polysorbate 20;

the solvent component comprises one or more substances independently selected from propylene glycol and polyethylene glycol; and the stabilizing agent component comprises xanthan gum.

In some embodiments, the pharmaceutical formulation comprises:

from about 35% to about 65% of water by weight of the formulation;

from about 2% to about 15% of an occlusive agent component by weight of the formulation;

from about 2% to about 8% of a stiffening agent component by weight of the formulation;

from about 5% to about 15% of an emollient component by weight of the formulation;

from about 1% to about 9% of an emulsifier component by weight of the formulation;

from about 0.05% to about 5% of a stabilizing agent component by weight of the formulation;

from about 10% to about 35% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 40% to about 60% of water by weight of the formulation;

from about 5% to about 10% of an occlusive agent component by weight of the formulation;

from about 2% to about 8% of a stiffening agent component by weight of the formulation;

from about 7% to about 12% of an emollient component by weight of the formulation;

from about 2% to about 6% of an emulsifier component by weight of the formulation;

from about 0.1% to about 2% of a stabilizing agent by weight of the formulation;

from about 15% to about 30% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 5% to about 10% of an occlusive agent component by weight of the formulation;

from about 3% to about 6% of a stiffening agent component by weight of the formulation;

from about 7% to about 13% of an emollient component by weight of the formulation;

from about 3% to about 5% of an emulsifier component by weight of the formulation;

from about 0.3% to about 0.5% of a stabilizing agent component by weight of the formulation;

from about 20% to about 25% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 5% to about 10% of an occlusive agent component by weight of the formulation;

from about 4% to about 7% of a stiffening agent component by weight of the formulation;

from about 7% to about 13% of an emollient component by weight of the formulation;

from about 4% to about 7% of an emulsifier component by weight of the formulation;

from about 0.3% to about 0.5% of a stabilizing agent component by weight of the formulation;

from about 20% to about 25% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

about 7% of an occlusive agent component by weight of the formulation;

from about 4.5% to about 5% of a stiffening agent component by weight of the formulation;

- about 10% of an emollient component by weight of the formulation;
- from about 4% to about 4.5% of an emulsifier component by weight of the formulation;
- about 0.4% of a stabilizing agent component by weight of the formulation;
- about 22% of a solvent component by weight of the formulation; and
- from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the combined amount of the stiffening agent component and the emulsifier component is at least about 8% by weight of the formulation.

In some embodiments:

- the occlusive agent component comprises a petrolatum;
- the stiffening agent component comprises one or more substances independently selected from one or more fatty alcohols;
- the emollient component comprises one or more substances independently selected from mineral oils and triglycerides;
- the emulsifier component comprises one or more substances independently selected from glyceryl fatty esters and sorbitan fatty esters;
- the stabilizing agent component comprises one or more substances independently selected from polysaccharides; and
- the solvent component comprises one or more substances independently selected from alkylene glycols and polyalkylene glycols.

In some embodiments:

- the occlusive agent component comprises white petrolatum;
- the stiffening agent component comprises one or more substances independently selected from cetyl alcohol and stearyl alcohol;
- the emollient component comprises one or more substances independently selected from light mineral oil, medium chain triglycerides, and dimethicone;
- the emulsifier component comprises one or more substances independently selected from glyceryl stearate and polysorbate 20;
- the stabilizing agent component comprises xanthan gum; and
- the solvent component comprises one or more substances independently selected from propylene glycol and polyethylene glycol.

In some embodiments, the pharmaceutical formulation further comprises an antimicrobial preservative component.

In some embodiments, the antimicrobial preservative component is present in an amount of about 0.05% to about 3% by weight of the formulation.

In some embodiments, the antimicrobial preservative component is present in an amount of about 0.1% to about 1% by weight of the formulation.

As used herein, the phrase "antimicrobial preservative component" is a substance or mixtures of substances which inhibits microbial growth in the formulation.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the pharmaceutical formulation further comprises a chelating agent component.

As used herein, the phrase "chelating agent component" refers to a compound or mixtures of compounds that has the ability to bind strongly with metal ions.

In some embodiments, the chelating agent component comprises edetate disodium.

(R)-3-(4-(7H-Pyrrolo[2,3-d]pyrimidin-4-yl)-1H-pyrazol-1-yl)-3-cyclopentylpropanenitrile can be prepared as described in U.S. Pat. No. 7,598,257 and U.S. Patent Publ. No. 2009/0181959, each of which is incorporated herein by reference in its entirety. The 1:1 phosphate salt of (R)-3-(4-(7H-pyrrolo[2,3-d]pyrimidin-4-yl)-1H-pyrazol-1-yl)-3-cyclopentylpropanenitrile can be prepared as described in U.S. Patent Publ. No. 2008/0312259, which is incorporated herein by reference in its entirety.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and *Journal of Pharmaceutical Science,* 66, 2 (1977), each of which is incorporated herein by reference in their entireties.

It will also be understood that compounds described herein may exist in solvated, for example hydrated, as well as unsolvated forms. It will further be understood that the present invention encompasses all such solvated forms of the compounds.

As used herein, "% by weight of the formulation" means the percent concentration of the component in the formulation is on weight/weight basis. For example, 1% w/w of component A=[(mass of component A)/(total mass of the formulation)]×100.

As used herein, "% by weight of the formulation on a free base basis" of (R)-3-(4-(7H-pyrrolo[2,3-d]pyrimidin-4-yl)-1H-pyrazol-1-yl)-3-cyclopentylpropanenitrile, or pharmaceutically acceptable salt thereof" means that the % w/w is calculated based on the weight of (R)-3-(4-(7H-pyrrolo[2,3-d]pyrimidin-4-yl)-1H-pyrazol-1-yl)-3-cyclopentylpropanenitrile in the total formulation. For example, "0.5% w/w on a free base basis" of (R)-3-(4-(7H-pyrrolo[2,3-d]pyrimidin-4-yl)-1H-pyrazol-1-yl)-3-cyclopentylpropanenitrile phosphate means that for 100 grams of total formulation, there are 0.66 grams of (R)-3-(4-(7H-pyrrolo[2,3-d]pyrimidin-4-yl)-1H-pyrazol-1-yl)-3-cyclopentylpropanenitrile phosphate in the formulation (which equates to 0.5 grams of the free base, (R)-3-(4-(7H-pyrrolo[2,3-d]pyrimidin-4-yl)-1H-pyrazol-1-yl)-3-cyclopentylpropanenitrile).

In some embodiments, the components are present in exactly the ranges specified (e.g., the term "about" is not present). In some embodiments, "about" means plus or minus 10% of the value.

As will be appreciated, some components of the pharmaceutical formulations described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids.

In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula —O-alkylene-. In some embodiments, the polyalkylene glycol is polyethylene glycol.

As used herein, the term, "sorbitan fatty ester" includes products derived from sorbitan or sorbitol and fatty acids and, optionally, poly(ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE(20) sorbitan monolaurate), 21 (POE(4) sorbitan monolaurate), 40 (POE(20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE (20) sorbitan monooleate), 80K (POE(20) sorbitan monooleate), 81 (POE (5) sorbitan monooleate), and 85 (POE(20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula —O- alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula $—O—CH_2—CH_2—$. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Methods

The pharmaceutical formulations of the invention are useful in treating skin disorders. In some embodiments, the skin disorder is an autoimmune bullous skin disorder such as pemphigus vulgaris (PV) or bullous pemphigoid (BP). In some embodiments, the skin disorder is psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of the topical formulations of the invention together with the agent causing unwanted sensitization can be helpful in treating such unwanted sensitization or dermatitis.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anticancer drugs such as gefitinib, cetuximab, erlotinib, and the like. The formulations of the invention can be administered systemically or topically (e.g., localized to the vicinity of the dermatitis) in combination with (e.g., simultaneously or sequentially) the pharmaceutical agent having the undesirable dermatological side effect. In some embodiments, the formulation of the invention can be administered topically together with one or more other pharmaceuticals, where the other pharmaceuticals when topically applied in the absence of a formulation of the invention cause contact dermatitis, allergic contact sensitization, or similar skin disorder. Accordingly, formulation of the invention include topical formulations further comprising an additional pharmaceutical agent which can cause dermatitis, skin disorders, or related side effects.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the formulations of the present invention for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the formulations of the invention can be used in combination with one or more other kinase inhibitors including imatinib, particularly for treating patients resistant to imatinib or other kinase inhibitors.

In some embodiments, a corticosteroid such as dexamethasone is administered to a patient in combination with the compound of the invention where the dexamethasone is administered intermittently as opposed to continuously.

Labeled Compounds and Assay Methods

Another aspect of the present invention relates to formulations comprising a labeled active compound (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes formulations of an isotopically-labeled compound. An "isotopically" or "radio-labeled" compound is a compound where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Kits

The present invention also includes pharmaceutical kits useful, for example, in the treatment or prevention of JAK-associated diseases or disorders, such as cancer, which include one or more containers containing a pharmaceutical formulation of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some embodiments, the present invention provides pharmaceutical formulations comprising the components specified in the example formulations (e.g., Example 3), wherein the components are present in about the amounts in Tables 2-5.

EXAMPLES

Example 1: (3R)-and (3S)-3-Cyclopentyl-3-[4-(7H-pyrrolo[2,3-d]pyrimidin-4-yl)-1H-pyrazol-1-yl]propanenitrile

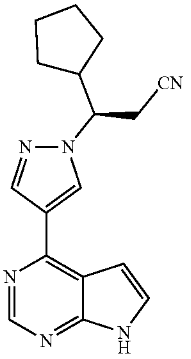

and

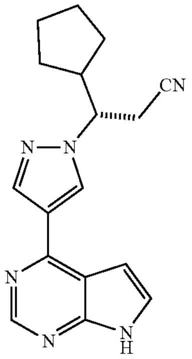

Step 1. (2E)-and (2Z)-3-Cyclopentylacrylonitrile

To a solution of 1.0 M potassium tert-butoxide in THF (235 mL) at 0° C. was added dropwise a solution of diethyl cyanomethylphosphonate (39.9 mL, 0.246 mol) in THF (300 mL). The cold bath was removed and the reaction was warmed to room temperature followed by recooling to 0° C., at which time a solution of cyclopentanecarbaldehyde (22.0 g, 0.224 mol) in THF (60 mL) was added dropwise. The bath was removed and the reaction warmed to ambient temperature and stirred for 64 hours. The mixture was partitioned between diethyl ether and water, the aqueous was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%).

$^{1}H$ NMR (400 MHz, $CDCl_3$): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3S)-3-Cyclopentyl-3-[4-(7-[2-(trimethylsilyl)ethoxy]methyl-7H-pyrrolo[2,3-d]pyrimidin-4-yl)-1H-pyrazol-1-yl]propanenitrile To a solution of 4-(1H-pyrazol-4-yl)-7-[2-(trimethylsilyl)ethoxy]methyl-7H- pyrrolo[2,3-d]pyrimidine (15.0 g, 0.0476 mol) in ACN (300 mL) was added 3-cyclopentylacrylonitrile (15 g, 0.12 mol) (as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The aqueous layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer.

$^1$H NMR (300 MHz, $CDCl_3$): δ 8.85 (s, 1H), 8.32 (s, 2H), 7.39 (d, 1H), 6.80 (d, 1H), 5.68 (s, 2H), 4.26 (dt, 1H), 3.54 (t, 2H), 3.14 (dd, 1H), 2.95 (dd, 1H), 2.67-2.50 (m, 1H), 2.03-1.88 (m, 1H), 1.80-1.15 (m, 7H), 0.92 (t, 2H), -0.06 (s, 9H); MS(ES):437 (M+1).

Step 3. (3R)- and (3S)-3-Cyclopentyl-3-[4-(7H-pyrrolo[2,3-d]pyrimidin-4-yl)-1H-pyrazol-1-yl]propanenitrile To a solution of 3-cyclopentyl-3-[4-(7-[2-(trimethylsilyl) ethoxy]methyl-7H-pyrrolo[2,3-d]pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much as possible of the TFA. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS (C18 eluting with a gradient of $ACN/H_2O$ containing 0.15% $NH_4OH$) to afford product (2.68 g, 58%).

$^1$H NMR (400 MHz, $D_6$-dmso): δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES):307 (M+1).

Example 2: (R)-3-(4-(7H-pyrrolo[2,3-d]pyrimidin-4-yl)-1H-pyrazol-1-yl)-3-cyclopentylpropanenitrile phosphoric acid salt

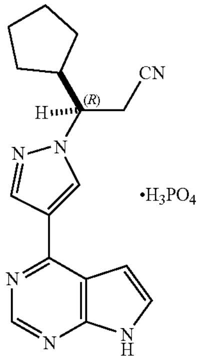

To a test tube was added (R)-3-(4-(7H-pyrrolo[2,3-d] pyrimidin-4-yl)-1H-pyrazol-1-yl)-3-cyclopentylpropanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg).

The phosphoric acid salt was shown to be a 1:1 salt by $^1$H NMR and crystallinity was confirmed by X-ray powder diffraction (XRPD). Differential scanning calorimetry (DSC) gave a sharp melting peak at about 198.66° C. The product showed little weight loss up to 200° C. by TGA.

Example 3: Preparation of Oil-In-Water Cream Formulations of (R)-3-(4-(7H-pyrrolo[2,3-d]pyrimidin-4-yl)-1H-pyrazol-1-yl)-3-cyclopentylpropanenitrile phosphoric acid salt An oil-in-water cream formulation was prepared for (R)-3-(4-(7H-pyrrolo[2,3-d]pyrimidin-4-yl)-1H-pyrazol-1-yl)-3-cyclopentylpropanenitrile phosphoric acid salt (Example 2) at 0.5, 1.0 and 1.5% by weight of the formulation (free base equivalent).

The compositions for a 15 gram tube are provided in Table 2 below. The formulation for three strengths were identical except for adjustments to the purified water quantity based on the amount of active ingredient. All excipients used in the formulation were compendial grade (ie, USP/NF or BP) or are approved for use in topical products.

The quantitative formulae for representative 400 kg batches of the cream formulation for Example 2 at 0.5, 1.0 and 1.5% are also provided in Tables 3, 4, and 5, respectively.

TABLE 2

| FORMULA | | | Percentage of Total | Grams/ |
|---|---|---|---|---|
| PHASE | COMPONENT | Function | (% w/w) | Tube |
| Paraben | Propylene Glycol USP | Solvent | 10.00 | 1.5 |
| | Methyl Paraben NF | Antimicrobial preservative | 0.10 | 0.015 |
| | Propyl Paraben NF | Antimicrobial preservative | 0.05 | 0.0075 |
| Xanthan Gum | Propylene Glycol USP | Solvent | 5.00 | 0.75 |
| | Xanthan Gum NF | Suspending, stabilizing, viscosity-increasing agent | 0.40 | 0.06 |
| Oil | Light Mineral Oil NF | Emollient, solvent | 4.00 | 0.6 |
| | Glyceryl Stearate SE | Emulsifier | 3.00 | 0.45 |
| | Polysorbate 20 NF | Emulsifying/ stabilizing agent | 1.25 | 0.1875 |
| | White Petrolatum USP | Occlusive agent | 7.00 | 1.05 |
| | Cetyl Alcohol NF | Stiffening agent, consistency improver | 3.00 | 0.45 |
| | Stearyl Alcohol NF | Stiffening agent | 1.75 | 0.2625 |
| | Dimethicone 360 NF | Skin protectant | 1.00 | 0.15 |
| | Medium Chain Triglyceride NF | Emollient, solvent | 5.00 | 0.75 |

TABLE 2-continued

| FORMULA | | | Percentage of Total | Grams/ |
|---|---|---|---|---|
| PHASE | COMPONENT | Function | (% w/w) | Tube |
| Aqueous/ Active | Purified Water USP | Solvent | 50.24-48.92 | 7.536-7.338 |
| | Edetate Disodium USP | Chelating agent | 0.05 | 0.0075 |
| | Polyethylene Glycol USP | Solvent | 7.00 | 1.05 |
| | Example 2 * | Active | 0.66-1.98 | 0.099-0.297 |
| Final | Phenoxyethanol BP | Antimicrobial preservative | 0.50 | 0.075 |
| | Total | | 100.00% | 15 |

* 1.32% of Example 2 is equivalent to 1.0% of (R)-3-(4-(7H-pyrrolo[2,3-d]pyrimidin-4-yl)-1H-pyrazol-1-yl)-3-cyclopentylpropanenitrile free base

TABLE 3

| Ingredient | Kilograms | Percentage (w/w) |
|---|---|---|
| (R)-3-(4-(7H-pyrrolo[2,3-d]pyrimidin-4-yl)-1H-pyrazol-1-yl)-3-cyclopentylpropanenitrile phosphoric acid salt (Example 2) | 2.64 (phosphate salt)/ 2.0 (free base) | 0.66 (phosphate salt)/ 0.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 201 | 50.25 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 4

| Ingredient | Kilograms | Percentage (w/w) |
|---|---|---|
| (R)-3-(4-(7H-pyrrolo[2,3-d]pyrimidin-4-yl)-1H-pyrazol-1-yl)-3-cyclopentylpropanenitrile phosphoric acid salt (Example 2) | 5.28 (phosphate salt)/ 4.0 (free base) | 1.32 (phosphate salt)/ 1.00 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |

TABLE 4-continued

| Ingredient | Kilograms | Percentage (w/w) |
|---|---|---|
| Purified Water USP (approximate) | 198.5 | 49.6 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 5

| Ingredient | Kilograms | Percentage (w/w) |
|---|---|---|
| (R)-3-(4-(7H-pyrrolo[2.3-d]pyrimidin-4-yl)-1H-pyrazol-1-yl)-3-cyclopentylpropanenitrile phosphoric acid salt (Example 2) | 7.92 (phosphate salt)/ 6.0 (free base) | 1.98 (phophate salt)/ 1.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 195.5 | 48.9 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

The oil-in-water cream formulations were synthesized according to the following procedure at either a 3.5 kg or 400 kg scale (when made at a 3.5 kg batch size, the amounts in Tables 3-5 were scaled appropriately). Some batches were subject to minor changes associated with scale-up, such as the size of mixing vessels and mixers. Generally, overhead mixer with high and low shear mixing blades are suitable for the process. FIG. 1 shows a flowchart representation of the process for making the oil-in-water formulation. The (R)-3-(4-(7H-pyrrolo[2,3-d]pyrimidin-4-yl)-1H-pyrazol-1-yl)-3-cyclopentylpropanenitrile is referred to as "API" throughout this application.

Procedure

1. A paraben phase was prepared by mixing methyl and propyl parabens with a portion of the propylene glycol (see % in Tables 2-5).
2. Next, a xanthan gum phase was prepared by mixing xanthan gum with propylene glycol (see % in Table 2-5).
3. An oil phase was then prepared by mixing light mineral oil, glyceryl stearate, polysorbate 20, white petrolatum, cetyl alcohol, stearyl alcohol, dimethicone and medium chain triglycerides. The phase is heated to 70-80° C. to melt and form a uniform mixture.
4. The aqueous phase was next prepared by mixing purified water, polyethylene glycol, and disodium EDTA. The phase is heated to 70-80° C.
5. The aqueous phase of step 4, paraben phase of step 1, and Example 2 (phosphate salt of API) were combined to form a mixture.

6. The xanthan gum phase from step 2 was then added to the mixture from step 5.
7. The oil phase from step 3 was then combined under high shear mixing with the mixture from step 6 to form an emulsion.
8. Phenoxyethanol was then added to the emulsion from step 7. Mixing was continued, and then the product was cooled under low shear mixing.

More consistent batches at larger scales (e.g., 140 kg) could be obtained by adding Example 2 gradually to the aqueous phase and then combining with the other phases. Similarly, more consistent batches could be obtained by slower cooling (e.g., by using room temperature water in the outer jacket of the reactor, rather than lower temperature water.

Analytical Results for Cream Formulations and Stability Studies

A. Methods

The appearance of the cream was visually inspected. Viscosity was measured using a Brookfield viscometer at 25° C. The pH was measured on the final cream formulation. The microbial limit testing is performed as per USP. The fill weight is analyzed as an in-process test during filling of the cream into tubes.

Assay, related substances, identity and content uniformity were determined in the formulation by a gradient reverse-phase HPLC with UV detection at 294 nm. A Waters HPLC was used with a Zorbax SB-C18 column (3.5 µm, 4.6×150 mm) at a flow rate of 1.0 mL/minute, temperature of 40° C. using Mobile Phase A of 2 mL of TFA into 4 L of Water (0.05% TFA), or Mobile Phase B of 2 mL of TFA into 4 L of methanol (0.05% TFA).

B. Results

Results are shown below for a 3.5 kg batches at 0.5%, 1% and 1.5% strength of Example 2 (free base basis (API)) (Table 6).

TABLE 6

| Test | Acceptance Criteria | Strength | | | | |
|---|---|---|---|---|---|---|
| | | Placebo | | 0.5% w/w | 1.0% w/w | 1.5% w/w |
| Appearance | Smooth, white emulsion | Conforms | | Conforms | Conforms | Conforms |
| pH | Report results | 6.5 | | 3.6 | 3.3 | 3.1 |
| Viscosity | Report results | 96,500 | | 66,500 | 64,800 | 72,900 |
| API Assay (%) | 90.0-110.0% | N/A | | 100.0 | 102.0 | 102.0 |
| API Related Substances | Report results | ND* | | ND* | ND* | ND* |
| Content Uniformity testing | 90-110% RSD: ≤5% | Top | N/A | 100 | 101 | 101 |
| | | | | 100 | 101 | 101 |
| | | Middle | N/A | 100 | 101 | 102 |
| | | | | 100 | 102 | 103 |
| | | Bottom | N/A | 100 | 102 | 103 |
| | | | | 100 | 102 | 102 |
| | | Avg. | N/A | 100 | 102 | 102 |
| | | RSD % | | 0.0 | 0.5 | 0.8 |

The stability data from batches of the cream formulation at 0.5, 1.0 and 1.5% w/w strength stored in 15 gram aluminum tubes is provided in Tables 7-10 and 19-20. Further, stability data from batches of the cream formulation at 0.5, 1.0 and 1.5% w/w strength packaged in amber glass jars (2 oz. with teflon cap) is provided in Tables 13-17, while longer stability data for the 1.0% w/w formulation packaged in 16 oz. amber glass jars is provided in Tables 11-12. The preliminary stability data for the drug product did not show any chemical instability after 3 months of storage at 25° C./60% RH and 40° C./75% RH in either packaging configuration. A change in viscosity is seen following 3months at 40° C./75% RH for formulation stored in amber glass jars. However, physical inspection of the product did not indicate any phase separation.

Acceptance criteria are shown below.

| Test | Acceptance Criteria |
|---|---|
| Appearance | Smooth, white cream |
| pH | Report results |
| Weight Loss | Report results |
| Viscosity (cps) | Report results |
| API Assay (%) | 90.0-110.0% of label claim |
| API Related Substances (RRT:Area %) | Report results |
| Total Related Substances (RRT:Area %) | Report results |
| MLT (Objectionable organisms) | Absent/1 g |
| MLT (*P. Aeruginosa*) | Absent/1 g |
| MLT (*S. Aureus*) | Absent/1 g |
| MLT (Total Aerobic) | NMT 100 CFU/g |
| MLT (Total Yeast and Molds) | NMT 10 CFU/g |

TABLE 7

Stability Data for 0.5% w/w Cream at 25° C./60% RH (15 aluminum gram tubes)

| Test | Time (Months) 0 | 1 | 3 | 6 |
|---|---|---|---|---|
| Appearance | Conforms | Conforms | Conforms | Conforms |
| pH | 3.6 | 3.6 | 3.6 | 3.6 |
| Weight Loss | NA | NA | 0.0 | 0.0 |
| Viscosity (cps) | 23400 | 29900 | 25400 | 24900 |
| API Assay (%) | 103.7 | 107.2 | 102.5 | 105.9 |
| API Related Substances (RRT:Area %) | ND | ND | 1.09:0.15 1.18:0.19 | ND |

TABLE 7-continued

Stability Data for 0.5% w/w Cream at 25° C./60% RH (15 aluminum gram tubes)

| | | | | |
|---|---|---|---|---|
| Total Related Substances (RRT:Area %) | NA | NA | 0.34 | NA |
| MLT (Objectionable organisms) | Absent/1 g | NA | Absent/1 g | Absent/1 g |
| MLT (*P. Aeruginosa*) | Absent/1 g | NA | Absent/1 g | Absent/1 g |
| MLT (*S. Aureus*) | Absent/1 g | NA | Absent/1 g | Absent/1 g |
| MLT (Total Aerobic) | <10 | NA | <10 | <10 |
| MLT (Total Yeast and Molds) | <10 | NA | <10 | <10 |

| | Time (Months) | | | |
|---|---|---|---|---|
| Test | 9 | 12 | 18 | 24 |
| Appearance | Conforms | Conforms | Conforms | Conforms |
| pH | 3.5 | 3.5 | 3.5 | 3.6 |
| Weight Loss | 0.0 | 0.0 | 0.0 | 0.0 |
| Viscosity (cps) | 26000 | 23000 | 20900 | 22500 |
| API Assay (%) | 105.4 | 105.7 | 104.4 | 104.0 |
| API Related Substances (RRT:Area %) | 1.10:0.10 | 1.09:0.14 | 0.95:0.18<br>1.09:0.20 | 0.11:0.24<br>0.95:0.23<br>1.11:0.08 |
| Total Related Substances (RRT:Area %) | 0.10 | 0.14 | 0.38 | 0.55 |
| MLT (Objectionable organisms) | Absent/1 g | Absent/1 g | NA | Absent/1 g |
| MLT (*P. Aeruginosa*) | Absent/1 g | Absent/1 g | NA | Absent/1 g |
| MLT (*S. Aureus*) | Absent/1 g | Absent/1 g | NA | Absent/1 g |
| MLT (Total Aerobic) | <10 | <10 | NA | <10 |
| MLT (Total Yeast and Molds) | <10 | <10 | NA | <10 |

TABLE 8

Stability Data for 0.5% w/w Cream at 40° C./75% RH (15 aluminum gram tubes)

| | Time (Months) | | | |
|---|---|---|---|---|
| Test | 0 mo. | 1 mo. | 3 mo. | 6 mo. |
| Appearance | Conforms | Conforms | Conforms | Conforms |
| pH | 3.6 | 3.6 | 3.6 | 3.5 |
| Weight Loss | N/A | N/A | 0.0 | 0.0 |
| Viscosity (cps) | 23400 | 26300 | 19800 | 18600 |
| API Assay (%) | 103.7 | 103.1 | 105.3 | 105.0 |
| API Related Substances (RRT:Area %) | N/D | N/D | 1.09:0.14 | 1.32: 0.21<br>1.39: 0.40 |
| Total Related Substances (RRT:Area %) | N/A | N/A | 0.14 | 0.61 |
| MLT (Objectionable organisms) | Absent/1 g | N/A | Absent/1 g | Absent/1 g |
| MLT (*P. Aeruginosa*) | Absent/1 g | N/A | Absent/1 g | Absent/1 g |
| MLT (*S. Aureus*) | Absent/1 g | N/A | Absent/1 g | Absent/1 g |
| MLT (Total Aerobic) | <10 | N/A | <10 | <10 |
| MLT (Total Yeast and Molds) | <10 | N/A | <10 | <10 |

TABLE 9

Stability Data for 1.5% w/w Cream at 25° C./60% RH (15 aluminum gram tubes)

| | Time (Months) | | | |
|---|---|---|---|---|
| Test | 0 | 1 | 3 | 6 |
| Appearance | Conforms | Conforms | Conforms | Conforms |
| pH | 3.2 | 3.1 | 3.2 | 3.1 |
| Weight Loss | NA | NA | 0.0 | 0.0 |
| Viscosity (cps) | 29433 | 35800 | 27400 | 26200 |
| API Assay (%) | 102.7 | 104.9 | 103.9 | 105.0 |
| API Related Substances (RRT:Area %) | ND | ND | 1.09:0.14 | ND |
| Total Related Substances (RRT:Area %) | NA | NA | 0.14 | ND |
| MLT (Objectionable organisms) | Absent/1 g | NA | Absent/1 g | Absent/1 g |
| MLT (*P. Aeruginosa*) | Absent/1 g | NA | Absent/1 g | Absent/1 g |
| MLT (*S. Aureus*) | Absent/1 g | NA | Absent/1 g | Absent/1 g |
| MLT (Total Aerobic) | <10 | NA | <10 | <10 |
| MLT (Total Yeast and Molds) | <10 | NA | <10 | <10 |

| | Time (Months) | | | |
|---|---|---|---|---|
| Test | 9 | 12 | 18 | 24 |
| Appearance | Conforms | Conforms | Conforms | Conforms |
| pH | 3.4 | 3.1 | 3.1 | 3.1 |
| Weight Loss | 0.0 | 0.0 | 0.0 | 0.0 |
| Viscosity (cps) | 25600 | 23800 | 21200 | 22200 |
| API Assay (%) | 103.7 | 105.0 | 102.6 | 103.0 |
| API Related Substances (RRT:Area %) | 1.10:0.12 | 1.09:0.13 | 1.09:0.21 | 0.20:0.09<br>0.95:0.07<br>1.11:0.10 |
| Total Related Substances (RRT:Area %) | 0.12 | 0.13 | 0.21 | 0.26 |
| MLT (Objectionable organisms) | Absent/1 g | Absent/1 g | NA | Absent/1 g |
| MLT (*P. Aeruginosa*) | Absent/1 g | Absent/1 g | NA | Absent/1 g |
| MLT (*S. Aureus*) | Absent/1 g | Absent/1 g | NA | Absent/1 g |
| MLT (Total Aerobic) | <10 | <10 | NA | <10 |
| MLT (Total Yeast and Molds) | <10 | <10 | NA | <10 |

TABLE 10

Stability Data for 1.5% w/w Cream at 40° C./75% RH (15 aluminum gram tubes)

| | Time (Months) | | | |
|---|---|---|---|---|
| Test | 0 mo. | 1 mo. | 3 mo. | 6 mo. |
| Appearance | Conforms | Conforms | Conforms | Conforms |
| pH | 3.2 | 3.1 | 3.2 | 3.1 |
| Weight Loss(g) | N/A | N/A | 0.0 | 0.0 |
| Viscosity (cps) | 29433 | 29800 | 22400 | 16300 |
| API Assay | 102.7 | 104.9 | 103.0 | 104.4 |
| API Related Substances RRT:Area % | N/D | N/D | 1.09:0.14 | 1.32:0.20<br>1.39:0.34 |
| Total Related Substance | N/A | N/A | 0.14 | 0.54 |
| Objectionable organisms | Absent/1 g | N/A | Absent/1 g | Absent/1 g |
| *P. Aeruginosa* | Absent/1 g | N/A | Absent/1 g | Absent/1 g |
| *S. Aureus* | Absent/1 g | N/A | Absent/1 g | Absent/1 g |
| Total Aerobic | <10 | N/A | <10 | <10 |
| Total Yeast and Molds | <10 | N/A | <10 | <10 |

TABLE 11

| Stability Data for 1.0% w/w Cream at 25° C./ 60% RH (16 oz. amber glass jars) | | | | |
|---|---|---|---|---|
| | Time (Months) | | | |
| Test | 0 | 3 | 6 | 12 |
| Appearance | Conforms | Conforms | Conforms | Conforms |
| pH | 3.5 | 3.3 | 3.3 | 3.3 |
| Viscosity (cps) | 35700 | 25600 | 21200 | 21400 |
| API Assay | 102.5 | 98.6 | 101.5 | 99.2 |
| API Related Substances (RRT:Area %) | 0.89:0.08 1.15:0.19 | 0.11:0.20 | ND | 0.88:NQ |
| Total Related Substances (RRT:Area %) | 0.27 | 0.20 | NA | 0.20 |
| MLT (Objectionable organisms) | Absent/1 g | Absent/1 g | Absent/1 g | Absent/1 g |
| MLT (*P. Aeruginosa*) | Absent/1 g | Absent/1 g | Absent/1 g | Absent/1 g |
| MLT (*S. Aureus*) | Absent/1 g | Absent/1 g | Absent/1 g | Absent/1 g |
| MLT (Total Aerobic) | <10 | <10 | <10 | <10 |
| MLT (Total Yeast and Molds) | <10 | <10 | <10 | <10 |

NA: Not applicable
ND: Not Detected
NQ: Not Quantifiable

TABLE 12

| Stability Data for 1.0% w/w Cream at 25° C./ 60% RH (16 oz. amber glass jars) | | |
|---|---|---|
| | Time (Months) | |
| Test | 0 | 6 |
| Appearance | Conforms | Conforms |
| pH | 3.5 | 3.2 |
| API Assay | 102.5 | 100.8 |
| API Related Substances (RRT:Area %) | 0.89:0.08 1.15:0.19 | ND |
| Total Related Substances (RRT:Area %) | 0.27 | ND |
| MLT (Objectionable organisms) | Absent/1 g | Absent/1 g |
| MLT (*P. Aeruginosa*) | Absent/1 g | Absent/1 g |
| MLT (*S. Aureus*) | Absent/1 g | Absent/1 g |
| MLT (Total Aerobic) | <10 | <10 |
| MLT (Total Yeast and Molds) | <10 | <10 |

TABLE 13

| Stability Data for 0.5% w/w Cream at 25° C./60% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.6 | 3.5 | 3.6 | 3.6 |
| Viscosity (cps) | Report results | 66500 | 71500 | 66000 | 56800 |
| API Assay (%) | 90.0-110.0% | 100.0 | 101.0 | 100.0 | 100.0 |
| Related Substances | Report results | ND* | ND* | ND* | ND* |

*Not detected

TABLE 14

| Stability Data for 0.5% w/w Cream at 40° C./75% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.6 | 3.6 | 3.5 | 3.6 |
| Viscosity (cps) | Report results | 66500 | 63900 | 51900 | 39000 |
| API Assay (%) | 90.0-110.0% | 100.0 | 99.0 | 98.0 | 102.0 |
| Related Substances | Report results | ND* | ND* | ND* | ND* |

*Not detected

TABLE 15

Stability Data for 1.0% w/w Cream at 25° C./60% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.3 | 3.2 | 3.2 | 3.3 |
| Viscosity (cps) | Report results | 64800 | 69300 | 61400 | 50500 |
| API Assay (%) | 90.0-110.0% | 102.0 | 102.0 | 103.0 | 102.5 |
| Related Substances | Report results | ND* | ND* | ND* | ND* |

*Not detected

TABLE 16

Stability Data for 1.0% w/w Cream at 40° C./75% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.3 | 3.2 | 3.2 | 3.3 |
| Viscosity (cps) | Report results | 64800 | 57900 | 55100 | 33500 |
| API Assay (%) | 90.0-110.0% | 102.0 | 102.0 | 101.0 | 103.0 |
| Related Substances | Report results | ND* | ND* | ND* | ND* |

*Not detected

TABLE 17

Stability Data for 1.5% w/w Cream at 25° C./60% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.1 | 2.9 | 3.1 | 3.2 |
| Viscosity (cps) | Report results | 72900 | 66600 | 62400 | 60300 |
| API Assay (%) | 90.0-110.0% | 101.7 | 101.7 | 101.7 | 104.3 |
| Related Substances | Report results | ND* | ND* | ND* | ND* |

*Not detected

TABLE 18

Stability Data for 1.5% w/w Cream at 40° C./75% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.1 | 3.1 | 3.1 | 3.2 |
| Viscosity (cps) | Report results | 72900 | 62500 | 53000 | 43800 |
| Assay (%) | 90.0-110.0% | 101.7 | 103.0 | 102.0 | 104.3 |
| Related Substances | Report results | ND* | ND* | ND* | ND* |

*Not detected

TABLE 19

| Stability Data for 1.0% w/w Cream at 25° C./60% RH (15 gram aluminum tubes) | | | |
|---|---|---|---|
| | Acceptance | Time (Months) | |
| Test | Criteria | 0 mo. | 3 mo. |
| Appearance | Smooth, white emulsion | Conforms | Conforms |
| pH | Report result | 3.3 | 3.2 |
| Assay (%) | 90.0-110.0% | 102.2 | 101.7 |
| Related Substances | Report results | ND* | ND* |

*Not detected

TABLE 20

| Stability Data for 1.0% w/w Cream at 40° C./75% RH (15 gram aluminum tubes) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white emulsion | Conforms | — | — | Conforms |
| pH | Report result | 3.3 | — | — | 3.2 |
| API Assay (%) | 90.0-110.0% | 102.2 | 103.5 | 103.8 | 101.7 |
| Related Substances | Report results | ND* | ND* | ND* | ND* |

*Not detected

Example 4: Solubility Studies

In order to determine the solubility of (R)-3-(4-(7H-pyrrolo[2,3-d]pyrimidin-4-yl)-1H-pyrazol-1-yl)-3-cyclopentylpropanenitrile (free base) or its phosphate salt, approximately 5 mL of a potential solvent was added to approximately 50 mg of the API or its salt at room temperature. The mixtures were suspended and rotated on a wheel. If the mixtures became clear solutions, more solid material was added. The suspensions were then suspended over 24 hours. The samples were filtered through 0.2 micron filters. The liquid portions were collected and diluted with 50/50 water methanol/water. The concentrations of the diluted samples were analyzed by HPLC. When the free base or salt was fairly insoluble, the results are approximate only.

TABLE 21

| Potential Solvent | Solubility of Phosphate Salt (mg/mL) | Solubility of Free Base (mg/mL) |
|---|---|---|
| Water | 2.7 | 2.0 |
| pH 4, citric buffer, 0.1M | 1.5 | 1.1 |
| pH 6, citric buffer, 0.1M | 0.2 | 0.15 |
| Ethanol | 7.3 | 5.5 |
| Isopropanol | 0.6 | 0.45 |
| Benzyl alcohol | 3 | 2.3 |
| Propylene glycol | 24 | 18.2 |
| PEG 200 | 23 | 17.4 |
| PEG 300 | 14 | 10.6 |
| Glycerin | 11 | 8.3 |
| Transcutol | 10 | 7.6 |
| Trolamine | 51 | 38.6 |
| Water/PEG 200 (50/50) | 23 | 17.4 |
| Water/glyercin (50/50) | 21 | 15.9 |
| Water/glycerin/trolamine (40/40/20) | 18 | 13.6 |

TABLE 21-continued

| Potential Solvent | Solubility of Phosphate Salt (mg/mL) | Solubility of Free Base (mg/mL) |
|---|---|---|
| Isopropyl myristate | <0.1 | 0.08 |
| Isosorbide dimethyl ether | 0.4 | 0.3 |
| Mineral oil | <0.1 | 0.08 |
| Olelyl alcohol | 0.1 | 0.08 |
| Dimethicone | <0.2 | 0.15 |
| $C_{12-15}$ alcohol benzoate | <0.2 | 0.15 |
| Caprylic triglyceride | <0.2 | 0.15 |

Example 5: Other Topical Formulations

Three different topical formulations incorporating the phosphate salt of (R)-3-(4-(7H-pyrrolo[2,3-d]pyrimidin-4-yl)-1H-pyrazol-1-yl)-3-cyclopentylpropanenitrile were also prepared. The compositions of a 1% w/w dispersed cream (water-in-oil formulation), 1% w/w anhydrous ointment, and 1% w/w lotion are summarized in Table 22 (percentages are on a free base basis). Each of the formulations with 1% w/w of the phosphate salt of the API were lower in viscosity as compared to placebo (in the placebo, the balance is water). While not wishing to be bound by any particular theory, the lower viscosity was believed to be due to electrolytic nature of the phosphate salt. Viscosities of the formulations and placebo over time are shown in Table 23. The 1% dispersed cream (water-in-oil formulation) showed syneresis after two and four weeks of aging at 40° C., while the 1% lotion and 1% solubilized cream formulations (oil-in-water formulations) did not show syneresis. The 1% solubilized cream formulation was generally higher in viscosity than the 1% lotion.

TABLE 22

| Ingredient | 1% w/w lotion | 1% w/w dispersed cream | 1% w/w ointment |
|---|---|---|---|
| Purified water USP | 52.03 | 39.48 | |
| Polyethylene glycol 200 USP | 7.00 | | |
| Example 2* | 1.32 | 1.32 | 1.32 |
| Disodium EDTA USP | 0.05 | 0.50 | |
| Phenoxyethanol BP | 0.50 | 0.50 | |
| Propylene glycol USP | 15.00 | 7.50 | |
| Xanthan Gum NF | 0.20 | | |
| Methylparaben NF | 0.10 | 0.10 | |
| Propylparaben NF | 0.05 | 0.05 | |
| Light mineral oil NF | 4.00 | 6.00 | |
| Glyceryl stearate SE FDA IIG | 2.00 | | |
| Polysorbate 20 NF | 1.00 | | |
| White Petrolatum USP | 7.00 | 5.00 | 78.68 |
| Cetyl Alcohol NF | 2.50 | | |
| Stearyl Alcohol NF | 1.25 | | |
| Dimethicone NF | 1.00 | 1.00 | |
| Caprilic/capric triglycerides FDA-IIG | 5.00 | 6.00 | |
| Sodium Chloride | | 0.05 | |
| Glycerin 99% USP | | 7.50 | |
| Sorbitol solution 70% USP | | 5.00 | |
| White Wax NF | | 1.50 | |
| Hydrogenated castor oil NF | | 1.50 | |
| Cyclomethicone NF | | 12.00 | |
| Polyglyceryl-3-diisostearate NF/BP | | 5.00 | |
| Cyclomethicone (D5) NF | | | 15.00 |
| Paraffin NF | | | 5.00 |
| Total | | | |

*1.32% of (R)-3-(4-(7H-pyrrolo[2,3-d]pyrimidin-4-yl)-1H-pyrazol-1-yl)-3-cyclopentylpropanenitrile phosphate salt is 1% of the free base.

TABLE 23

| Type of | Aging | | Viscosity | | Spindle/rpm | |
|---|---|---|---|---|---|---|
| Formulation | Time | Temp. | 1% w/w API | Placebo | 1% w/w API | Placebo |
| Solubilized cream* | Initial | | 99,400 | 195,600 | T-B/2.0 | T-C/2.5 |
| | 2 weeks | RT | 67,625 | 80,125 | 27/2.0 | 27/2.0 |
| | 4 weeks | RT | 65,875 | 82,750 | 27/2.0 | 27/2.0 |
| | 2 weeks | 5° C. | 73,125 | 55,250 | 27/2.0 | 27/2.0 |
| | 4 weeks | 5° C. | 86,000 | 70,125 | 27/2.0 | 27/2.0 |
| | 2 weeks | 40° C. | 46,375 | 41,875 | 27/2.0 | 27/2.0 |
| | 4 weeks | 40° C. | 47,500 | 50,125 | 27/2.0 | 27/2.0 |
| Lotion* | Initial | | 24,700 | 70,500 | T-A/4.0 | 27/2.0 |
| | 2 weeks | RT | 28,875 | 79,250 | 27/2.0 | 27/2.0 |
| | 4 weeks | RT | 32,750 | 73,875 | 27/2.0 | 27/2.0 |
| | 2 weeks | 5° C. | 31,750 | 70,250 | 27/2.0 | 27/2.0 |
| | 4 weeks | 5° C. | 34,750 | 75,750 | 27/2.0 | 27/2.0 |
| | 2 weeks | 40° C. | 28,250 | 44,250 | 27/2.0 | 27/2.0 |
| | 4 weeks | 40° C. | 29,125 | 53,000 | 27/2.0 | 27/2.0 |
| Dispersed cream | Initial | | 11,400 | 255,500 | 27/5.0 | 28/1.0 |
| | 2 weeks | RT | 8,850 | 204,500 | 27/5.0 | 28/1.0 |
| | 4 weeks | RT | 12,200 | 208,500 | 27/5.0 | 28/1.0 |
| | 2 weeks | 5° C. | 9,550 | 226,000 | 27/5.0 | 28/1.0 |
| | 4 weeks | 5° C. | 11,200 | 238,500 | 27/5.0 | 28/1.0 |
| | 2 weeks | 40° C. | Syneresis | 185,500 | 27/5.0 | 28/1.0 |
| | 4 weeks | 40° C. | Syneresis | 185,000 | 27/5.0 | 28/1.0 |

*No syneresis observed

Example 6: Skin Permeation Studies

The three different topical formulations in Example 5 (Table 20) and the cream formulation in Example 3 (Table 4) were evaluated for transport across human cadaver skin. The skin permeation data are summarized in Table 24. Significant variability was observed in the transport among the three replicates for each formulation. The variability in transport may be due in part to differences in skin samples (donor, region of the body, thickness, etc.). In general, the two cream formulations showed higher flux compared to the lotion or ointment. The cumulative amount of API transported for the ointment formulation was particularly low in comparison to the other three formulations and this, at least in part, could be due to poor spreadability of the ointment leading to decreased surface area for transport. As a result, the two cream formulations were selected for further development, one as an oil-in-water (see Example 3 above) and the other as a water-in-oil emulsion base. Based on the solubility of the drug substance, strengths containing 1.0, 1.5, and 2.0% w/w of (R)-3-(4-(7H-pyrrolo[2,3-d]pyrimidin-4-yl)-1H-pyrazol-1-yl)-3-cyclopentylpropanenitrile phosphate salt were developed for the oil-in water base cream (solubilized cream) and 1.0, 2.0, and 3.0% w/w were developed for the water-in oil base cream (dispersed cream). Procedures for the skin permeation studies are described below.

Human Cadaver Skin Transport Studies

The permeability of the API in topical formulations was studied using cadaver human skin samples and Franz diffusion cells. Dermatomed human cadaver skin was obtained from tissue banks while the Franz diffusion cells were custom made. The human cadaver skin samples, sized to fit between the donor and the receiver compartments, were positioned on the Franz diffusion cells. Topical formulations were weighed (20 mg) onto glassine paper, placed formulation side toward the skin and clamped into place. The dosing chamber was covered with parafilm. The reservoir side was filled using saline with 4% albumin. The reservoir was stirred and maintained at 37° C. using a dry block heater (Aungst B. Fatty Acid Skin Penetration Enhancers. Pharm. Res. 1989; 6(3):244-247). At 4 hours, a 1 mL sample was removed and replaced with 1 mL of saline +4% albumin. At 24 hours, the entire reservoir was collected. The tissue was examined visually for any hole or tear. The reservoir side samples were analyzed for concentrations of the API by a LC/MS assay.

Mouse Skin Transport Studies

The permeability of the API in topical formulations was studied using freshly excised mouse skin samples mounted in Franz diffusion cells. Balb/c mice were depilated using a waxing technique four days before the experiment. The morning of the experiment the mice were euthanized and as much of the depilated skin as possible was removed, rinsed and kept moist with 37° C. saline until use. The mouse skin samples, sized to fit between the donor and the receiver compartments, were positioned between the donor and the receiver compartments of the Franz diffusion cells. The opening of the Franz cell was 1 $cm^{2.}$ Topical formulations were weighed (20 mg) on to glassine paper, placed formulation side toward the skin and clamped into place. The dosing chamber was covered with parafilm. The reservoir side was filled using saline with 4% albumin. The reservoir was stirred and maintained at 37° C. using a dry block heater (Aungst 1989 (above). At 4 hours, a 1 mL sample was removed and replaced with 1 mL of saline +4% albumin. At 24 hours, the entire reservoir was collected. The tissue was examined visually for any hole or tear. The reservoir side samples were analyzed for concentrations of the API by a LC/MS assay.

TABLE 24

Transport of (R)-3-(4-(7H-pyrrolo[2,3-d]pyrimidin-4-yl)-1H-pyrazol-1-yl)-3-cyclopentylpropanenitrile from Topical Formulations across Human Cadaver Skin

| Strength, Type of Formulation | Human Cadaver Skin Sample | Cumulative amount over 24 h (μg) | Average cumulative amount at 24 h (μg) |
|---|---|---|---|
| 1% w/w | ABS #0510038 | 0.77 | 5.16 |
| Dispersed Cream | Asterand #52214A1 | 10.8 | |
| (see Example 5, | Asterand #46581A1 | 3.91 | |

TABLE 24-continued

Transport of (R)-3-(4-(7H-pyrrolo[2,3-d]pyrimidin-4-yl)-1H-pyrazol-1-yl)-3-cyclopentylpropanenitrile from Topical Formulations across Human Cadaver Skin

| Strength, Type of Formulation | Human Cadaver Skin Sample | Cumulative amount over 24 h (μg) | Average cumulative amount at 24 h (μg) |
|---|---|---|---|
| Table 20, above) | | | |
| 1% w/w Solubilized | ABS #0510038 | 0.21 | 3.73 |
| Cream | Asterand #52214A1 | 10.6 | |
| (see Example 3, | Asterand #46581A1 | 0.39 | |
| Table 4, above) | | | |
| 1% w/w Ointment | ABS #0510038 | 0.06 | 0.06 |
| (Anhydrous) | Asterand #52214A1 | 0.07 | |
| (see Example 5, | Asterand #46581A1 | 0.07 | |
| Table 20, above) | | | |
| 1% w/w Lotion | ABS #0510038 | 0.10 | 0.83 |
| (see Example 5, | Asterand #52214A1 | 1.96 | |
| Table 20, above) | Asterand #46581A1 | 0.42 | |

The effect of strength of solubilized or dispersed cream formulation on the transport of (R)-3-(4-(7H-pyrrolo[2,3-d]pyrimidin-4-yl)-1H-pyrazol-1-yl)-3-cyclopentylpropanenitrile across human cadaver skin was also examined and the data are summarized in Table 25. Increases in strength from 1% w/w to 3% w/w of the dispersed cream formulation (water-in-oil base) and 1% w/w to 2% w/w of the solubilized cream formulation (oil-in-water base) did not result in any significant change in transport of (R)-3-(4-(7H-pyrrolo[2,3-d]pyrimidin-4-yl)-1H-pyrazol-1-yl)-3-cyclopentylpropanenitrile, suggesting that the flux of (R)-3-(4-(7H-pyrrolo[2,3-d]pyrimidin-4-yl)-1H-pyrazol-1-yl)-3-cyclopentylpropanenitrile is not limited by the rate of release from each of these formulations.

TABLE 25

Transport of (R)-3-(4-(7H-pyrrolo[2,3-d]pyrimidin-4-yl)-1H-pyrazol-1-yl)-3-cyclopentylpropanenitrile from Increasing Strength Topical Formulations across Human Cadaver Skin

| Strength, Type of Formulation | Human Cadaver Skin Sample | Cumulative Amount over 24 h (μg) | Average Cumulative Amount at 24 h (μg) |
|---|---|---|---|
| 1% w/w Dispersed | ABS #0510038 | 1.26 | 2.29 |
| Cream | Asterand #42996A1 | 3.31 | |
| (water-in-oil base) | | | |
| 2% w/w Dispersed | ABS #0510038 | 1.79 | 1.68 |
| Cream | Asterand #42996A1 | 1.56 | |
| (water-in-oil base) | | | |
| 3% w/w Dispersed | ABS #0510038 | 1.40 | 1.81 |
| Cream | Asterand #42996A1 | 2.23 | |
| (water-in-oil base) | | | |
| 1% w/w | ABS #0510038 | 0.17 | 0.89 |
| Solubilized Cream | Asterand #42996A1 | 1.62 | |
| (see Example 3 above) | | | |
| 1.5% w/w | ABS #0510038 | 0.21 | 0.30 |
| Solubilized Cream | Asterand #42996A1 | 0.39 | |
| (see Example 3 above) | | | |
| 2% w/w | ABS #0510038 | 0.24 | 0.25 |
| Solubilized Cream | Asterand #42996A1 | 0.26 | |

The transport of (R)-3-(4-(7H-pyrrolo[2,3-d]pyrimidin-4-yl)-1H-pyrazol-1-yl)-3-cyclopentylpropanenitrile across freshly excised mouse skin was also evaluated using formulations that were employed in rodent pharmacology studies (Table 26). There was a general trend of increased permeability when the strength of the solubilized cream was increased from 0.5 to 1.5%, while such a trend was not seen with the dispersed formulation. For the solubilized cream, the average cumulative amount of (R)-3-(4-(7H-pyrrolo[2,3-d]pyrimidin-4-yl)-1H-pyrazol-1-yl)-3-cyclopentylpropanenitrile transported across mouse skin over 24 h was about twenty times higher than that seen with human cadaver skin studies (cumulative average of all experiments).

Based on the solubility of (R)-3-(4-(7H-pyrrolo[2,3-d]pyrimidin-4-yl)-1H-pyrazol-1-yl)-3-cyclopentylpropanenitrile phosphate, a maximum drug loading of 1.5% was possible with the oil-in-water (solubilized cream) formulation. Of the two creams formulated, the oil in water (solubilized cream) product exhibited better physical stability (see Table 21 above). It should be noted that strengths higher than 3% in the dispersed cream formulation and 2% in the solubilized cream formulation were not physically stable beyond several days of storage at controlled room temperature, as the drug substance crystallized out of solution. Based on these findings, coupled with skin permeability results, manufacturability data, and physical and chemical characterization data obtained for the early stage formulations, a solubilized cream with an oil-in water emulsion base (with a maximum strength of 1.5% w/w) was chosen for further development.

TABLE 26

Transport of Various Formulations of (R)-3-(4-(7H-pyrrolo[2,3-d]pyrimidin-4-yl)-1H-pyrazol-1-yl)-3-cyclopentylpropanenitrile across Freshly Excised Mouse Skin

| Strength, Formulation | Cumulative Amount over 24 h (μg) | Average Cumulative amount at 24 h (μg) |
|---|---|---|
| 1% w/w dispersed cream | 37.1 | 42.0 |
| (water-in-oil base) | 46.9 | |
| 1% w/w dispersed cream | 18.0 | 23.1 |
| (water-in-oil base) | 28.2 | |
| 3% w/w dispersed cream | 29.6 | 29.8 |
| (water-in-oil base) | 30.0 | |
| 0.5% w/w solubilized cream | 26.5 | 23.5 |
| (see Example 3 above) | 20.4 | |
| 1% w/w solubilized cream | 40.8 | 32.8 |
| (see Example 3 above) | 24.9 | |
| 1.5% w/w solubilized cream | 44.6 | 41.8 |
| (see Example 3 above) | 38.9 | |

Example 7: Clinical Treatment of Psoriasis with Formulations

Figure 2:
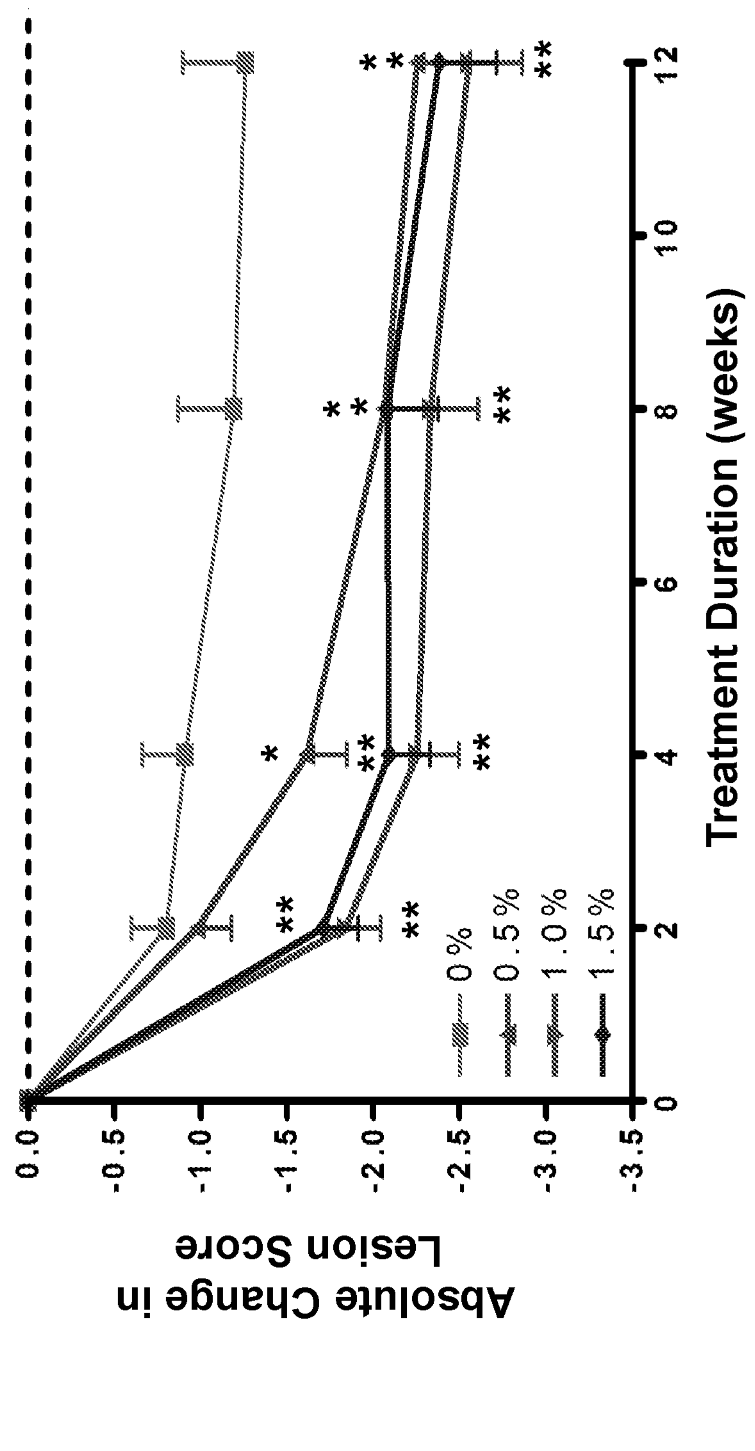
FIG. 2 depicts the change in lesion score for subjects with chronic plaque psoriasis treated with 0.5%, 1.0%, and 1.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis) as compared to treatment with placebo over a 12-week period (the dashed line is baseline).
Figure 3:
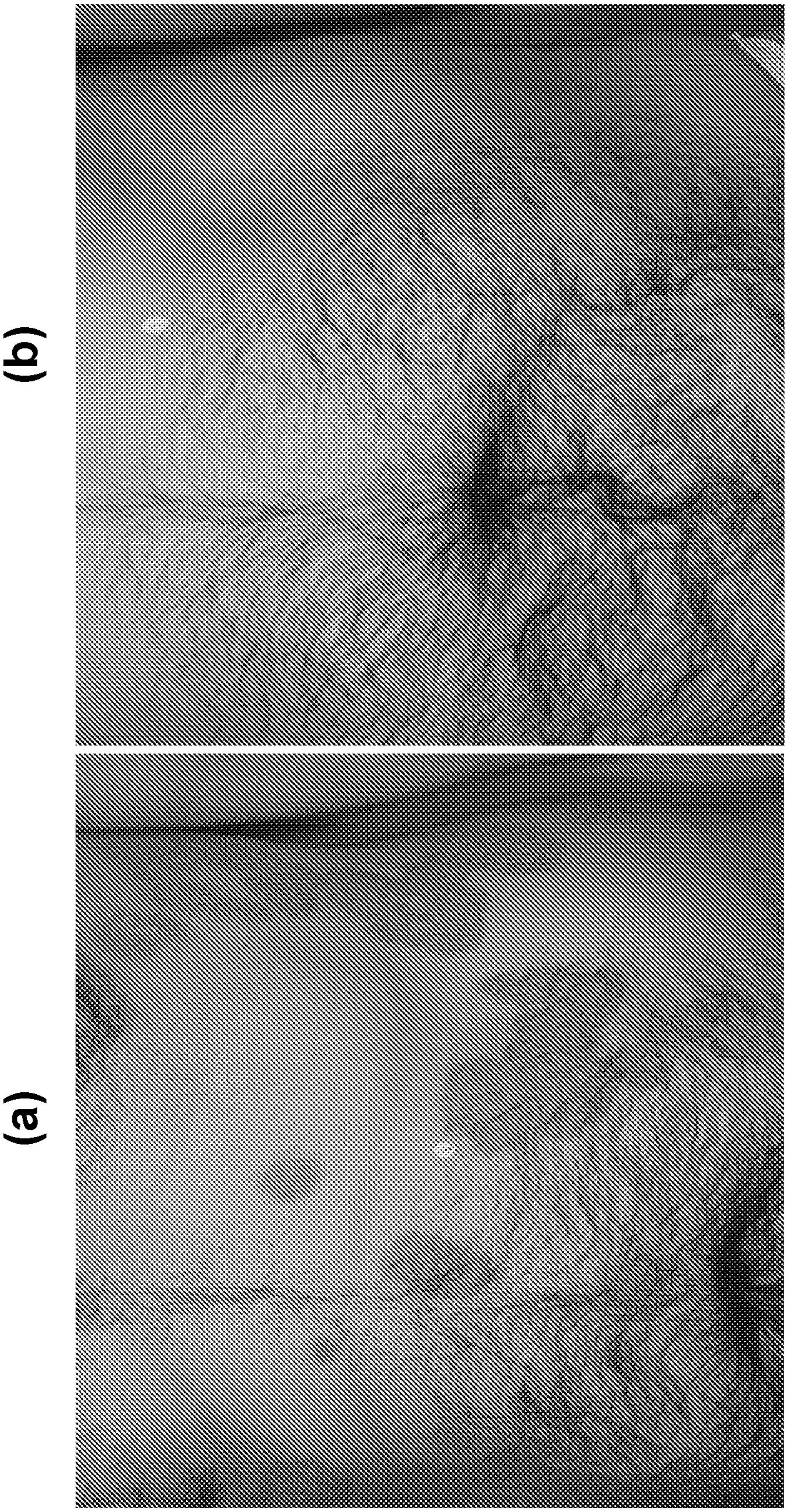
FIG. 3 shows photographs of subjects with chronic plaque psoriasis before (FIG. 3(*a*)) and after 84 days (FIG. 3(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 4:
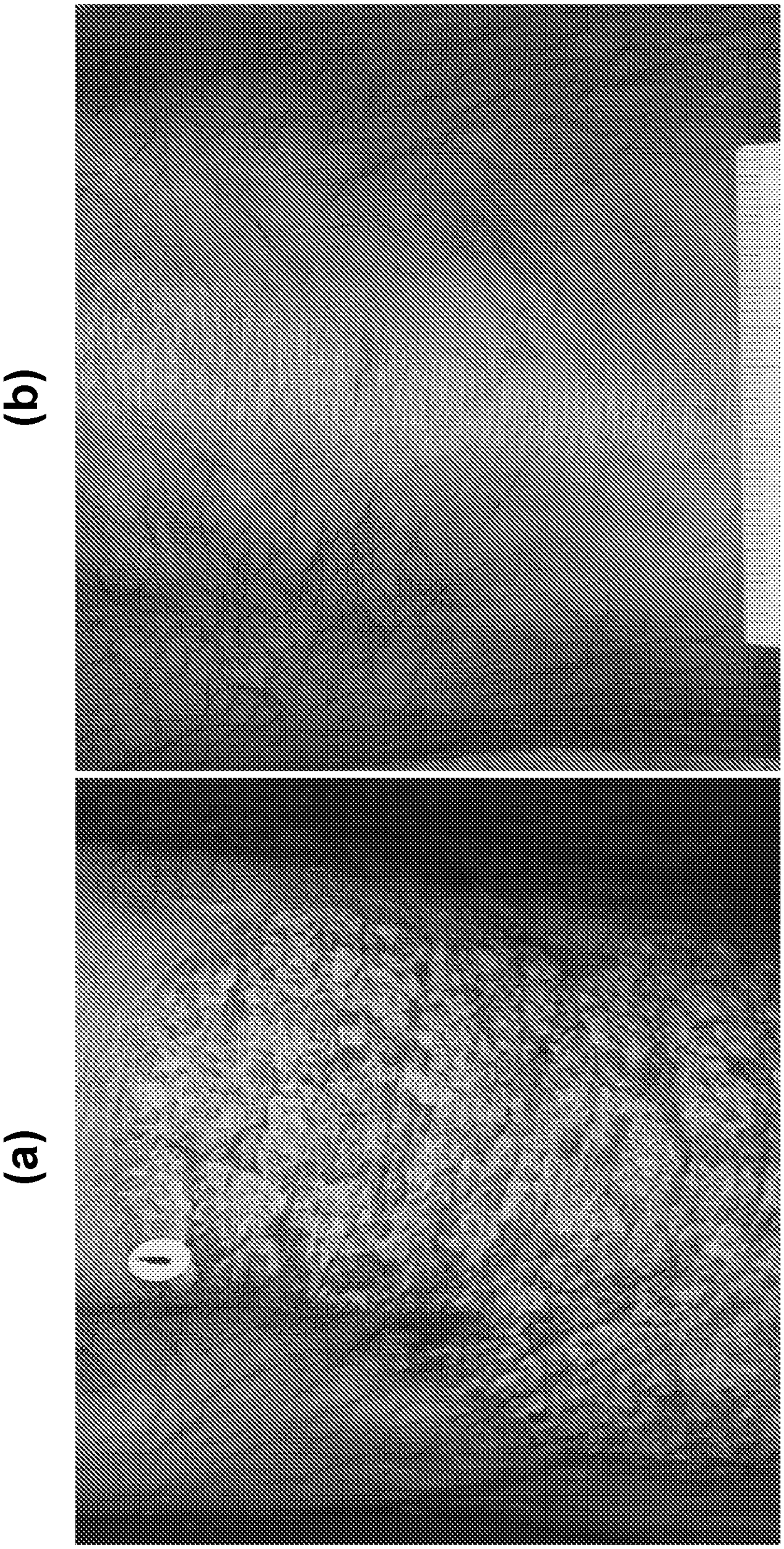
FIG. 4 shows photographs of subjects with chronic plaque psoriasis before (FIG. 4(*a*)) and after 84 days (FIG. 4(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 5:
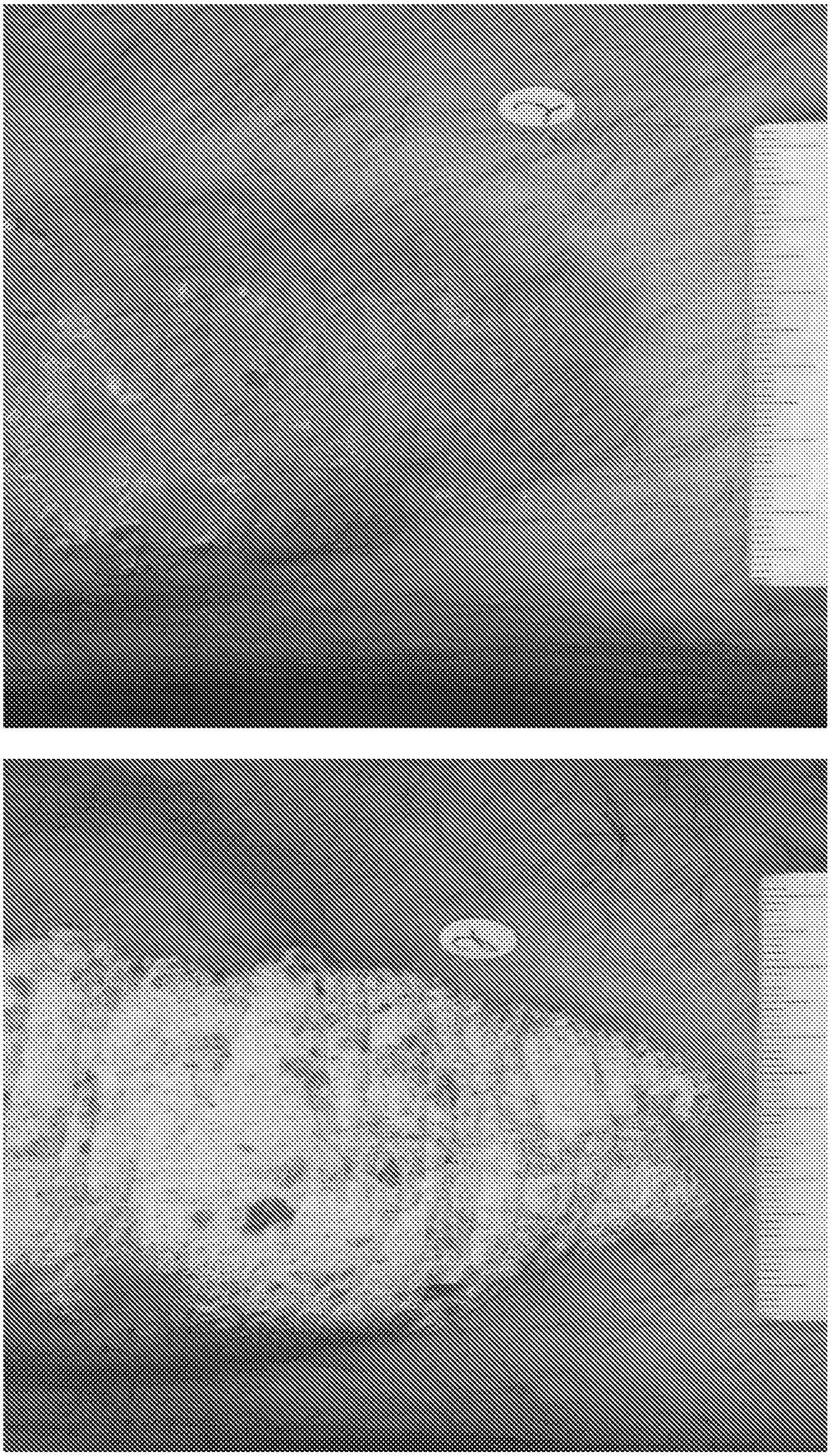
FIG. 5 shows photographs of subjects with chronic plaque psoriasis before (FIG. 5(*a*)) and after 84 days (FIG. 5(*b*)) of treatment with 1.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 6:
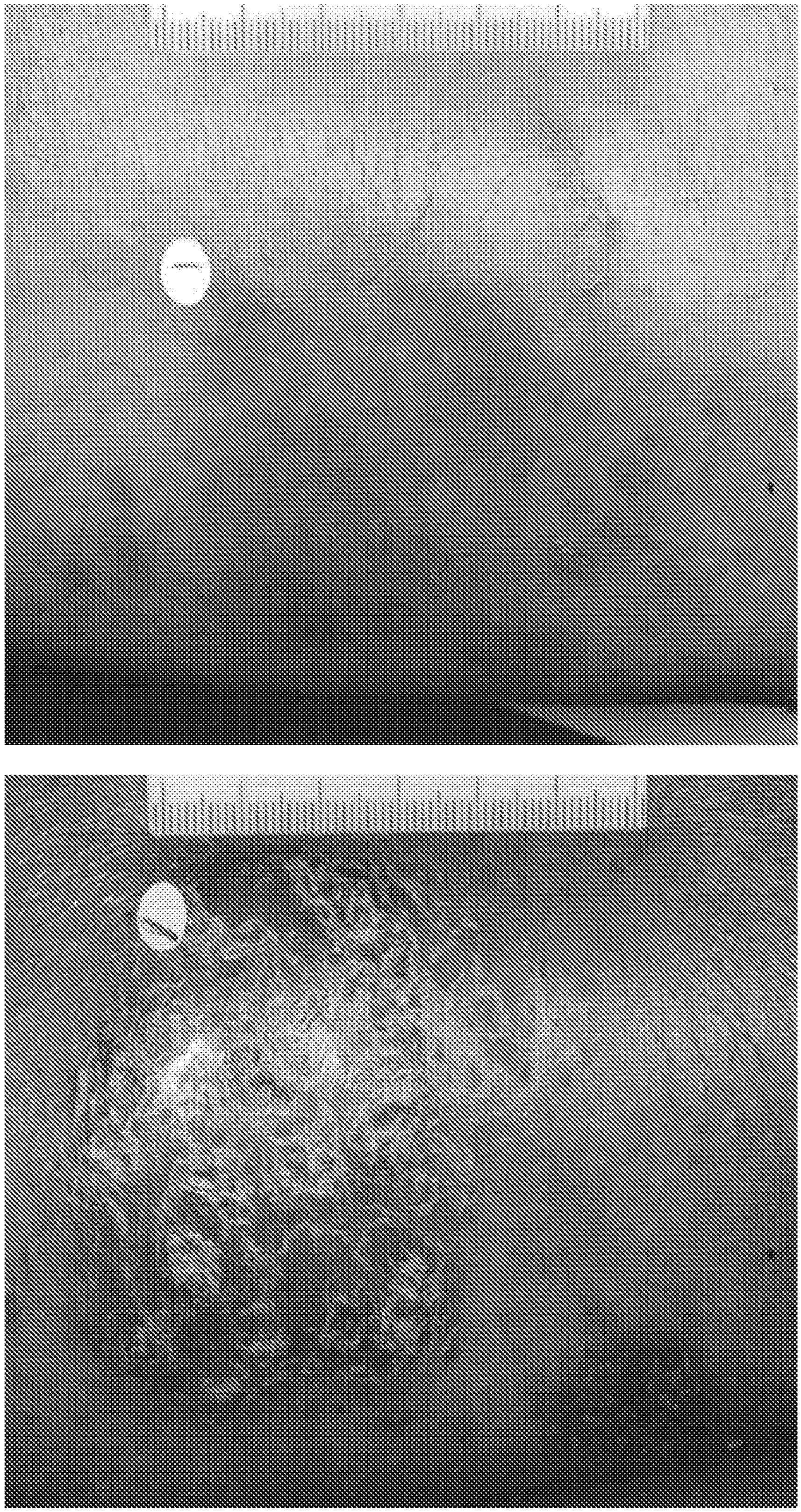
FIG. 6 shows photographs of subjects with chronic plaque psoriasis before (FIG. 6(*a*)) and after 84 days (FIG. 6(*b*)) of treatment with 0.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 7:
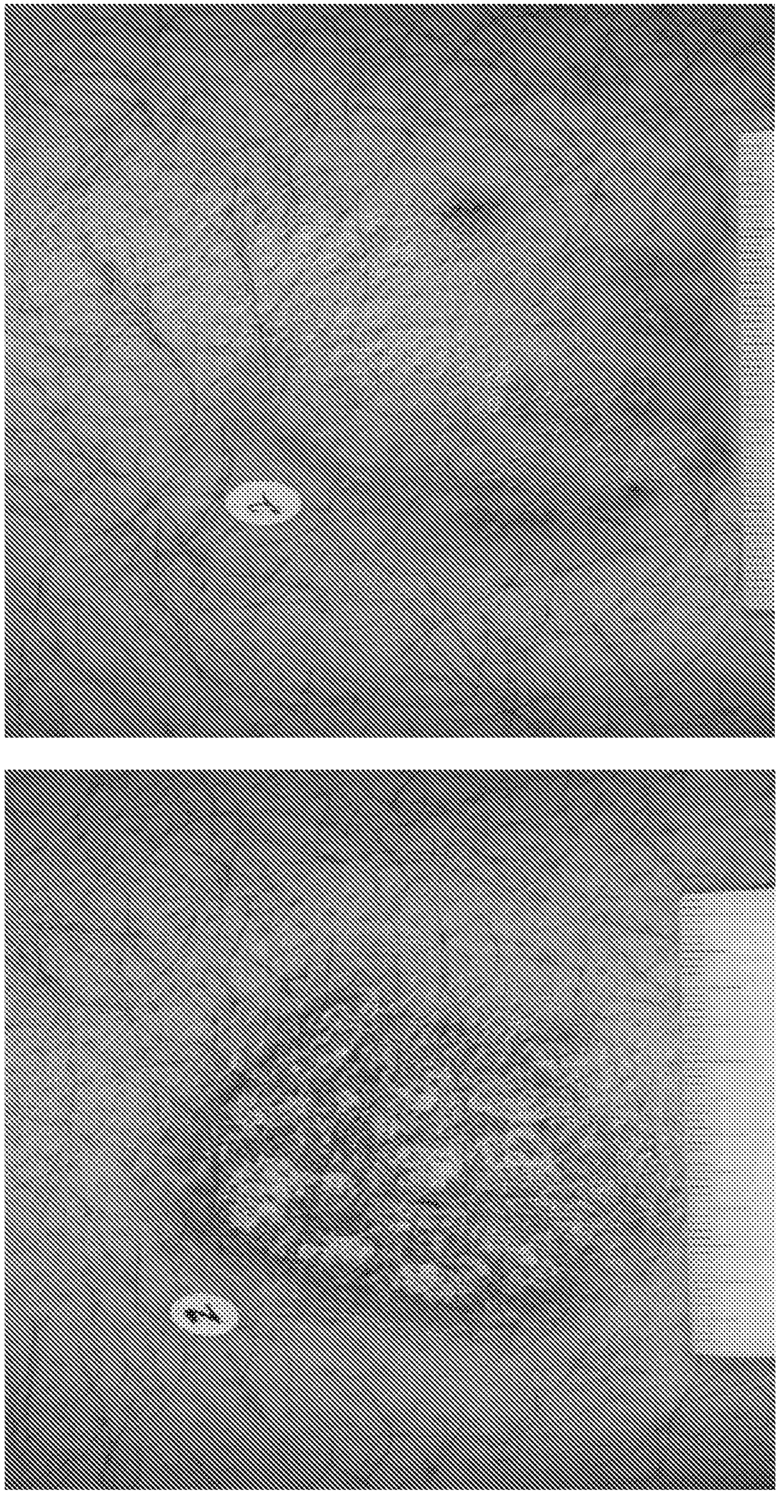
FIG. 7 shows photographs of subjects with chronic plaque psoriasis before (FIG. 7(*a*)) and after 84 days (FIG. 7(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).

Approximately 200 subjects with chronic plaque psoriasis were enrolled in a double-blind, placebo-controlled study. There were four dose groups, three active treatment groups and vehicle. The active treatment groups were treated with the 0.5%, 1.0%, and 1.5% w/w oil-in-water formulations (see Example 3 supra). Approximately 50 subjects were randomized into each treatment group. A thin layer of cream was applied once per day to up to 20% body surface area of plaque psoriasis. Treatment was applied for 84 days and efficacy measured by the change in total lesion score, a measurement scale which assesses the amount of erythema, scaling and thickness of the plaques (FIG. 2). 25% of patents randomized to 1% w/w or 1.5% w/w of the API had lesions that were clear or almost clear at week 12, versus 6% on vehicle.

At a subset of sites, photos were obtained from subjects who signed an informed consent for the photos. Pictures were obtained at baseline (prior to the first application of study treatment) and on day 84 (the last application day for study treatment) (see FIG. 3-7). These photos are representative of a subset of the subjects who were treated with the oil-in-water formulations.

Example 8: Murine Skin Contact Delayed Hypersensitivity Response Test

The formulations described herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 Jan; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 Jan;38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two hours after the challenge, ears are measured again. Treatment with the test formulations is given throughout the sensitization and challenge phases (day −1 to day 7) or prior to and throughout the challenge phase (usually afternoon of day 4 to day 7). Treatment of the test compounds (in different concentration) is administered topically (topical application of the treatment to the ears). Efficacies of the test formulations are indicated by a reduction in ear swelling comparing to the situation without the treatment. Compounds causing a reduction of 20% or more are considered efficacious. In some experiments, the mice are challenged but not sensitized (negative control).

The inhibitive effect (inhibiting activation of the JAK-STAT pathways) of the test formulations can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test formulations, vehicle, or dexamethasone (a clinically efficacious treatment for psoriasis), or without any treatment, in the DTH model for comparisons. Test formulations and the dexamethasone can produce similar transcriptional changes both qualitatively and quantitatively, and both the test formulations and dexamethasone can reduce the number of infiltrating cells. Topical administration of the test compounds can produce inhibitive effects, i.e., reduction in the number of infiltrating cells and inhibition of the transcriptional changes.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A pharmaceutical formulation for topical skin application, wherein the formulation is an oil-in-water emulsion, the formulation comprising:

from 35% to 65% by weight of the formulation of water;

from 10% to 40% by weight of the formulation of a mixture of petrolatum, $C_{16-18}$ fatty alcohols, mineral oil, a triglyceride, and a silicone oil;

from 2% to 6% by weight of the formulation of a mixture of a glyceryl fatty ester and a sorbitan fatty ester;

from 0.05% to 5% by weight of the formulation of a polysaccharide;

from 10% to 35% by weight of the formulation of a mixture of an alkylene glycol and a polyalkylene glycol; and from 0.5%-1.5% of (R)-3-cyclopentyl-3-[4-(7H-pyrrolo [2,3-d] pyrimidin-4-yl)-1H-pyrazol-1-yl] propanenitrile phosphoric acid salt by weight of the formulation on a free base basis.

2. The formulation according to claim 1, wherein:

the petroleum is white petrolatum;

the $C_{16-18}$ fatty alcohols are a mixture of cetyl alcohol and stearyl alcohol;

the mineral oil is light mineral oil;

the glyceride is medium chain triglycerides;

the silicone oil is dimethicone;

the glyceryl fatty ester is glyceryl stearate;

the sorbitan fatty ester is polysorbate 20;

the polysaccharide is xanthan gum;

the alkylene glycol is propylene glycol; and the polyalkylene glycol is polyethylene glycol.

3. The formulation according to claim 1, wherein:

the petroleum is white petrolatum;

the $C_{16-18}$ fatty alcohols are a mixture of cetyl alcohol and stearyl alcohol;

the mineral oil is light mineral oil;

the glyceride is medium chain triglycerides;

the silicone oil is dimethicone;

the glyceryl fatty ester is glyceryl stearate SE;

the sorbitan fatty ester is polysorbate 20;

the polysaccharide is xanthan gum;

the alkylene glycol is propylene glycol; and the polyalkylene glycol is polyethylene glycol 200.

4. The formulation according to claim 2, further comprising:

a chelating agent component; and from 0.05% to 3% by weight of the formulation of an antimicrobial preservative component.

5. The formulation of claim 3, further comprising:

0.1% by weight of the formulation of methyl paraben;

0.05% by weight of the formulation of propyl paraben;

0.05% by weight of the formulation of edetate disodium; and 0.5% by weight of the formulation of phenoxyethanol.

6. The formulation according to claim 1, wherein:

the water comprises from 40% to 60% by weight of the formulation;

the mixture of petrolatum, $C_{16-18}$ fatty alcohols, mineral oil, a glyceride, and a silicone oil comprises from 17% to 27% by weight of the formulation;

the mixture of a glyceryl fatty ester and a sorbitan fatty ester comprises from 3% to 5% by weight of the formulation;

the polysaccharide comprises from 0.1% to 2% by weight of the formulation; and
the mixture of an alkylene glycol and a polyalkylene glycol comprises from 15% to 30% by weight of the formulation.

7. The formulation according to claim 6, wherein:
the petroleum is white petrolatum;
the $C_{16-18}$ fatty alcohols are a mixture of cetyl alcohol and stearyl alcohol;
the mineral oil is light mineral oil;
the glyceride is medium chain triglycerides;
the silicone oil is dimethicone;
the glyceryl fatty ester is glyceryl stearate;
the sorbitan fatty ester is polysorbate 20;
the polysaccharide is xanthan gum;
the alkylene glycol is propylene glycol; and
the polyalkylene glycol is polyethylene glycol.

8. The formulation according to claim 6, wherein:
the petroleum is white petrolatum;
the $C_{16-18}$ patty alcohols are a mixture of cetyl alcohol and stearyl alcohol;
the mineral oil is light mineral oil;
the glyceride is medium chain triglycerides;
the silicone oil is dimethicone;
the glyceryl fatty ester is glyceryl stearate SE;
the sorbitan fatty ester is polysorbate 20;
the polysaccharide is xanthan gum;
the alkylene glycol is propylene glycol; and
the polyalkylene glycol is polyethylene glycol 200.

9. The formulation according to claim 7, further comprising:
a chelating agent component; and
from 0.05% to 3% by weight of the formulation of an antimicrobial preservative component.

10. The formulation of claim 8, further comprising:
0.1% by weight of the formulation of methyl paraben;
0.05% by weight of the formulation of propyl paraben;
0.05% by weight of the formulation of edetate disodium; and
0.5% by weight of the formulation of phenoxyethanol.

11. The formulation according to claim 1, wherein:
the water comprises from 45% to 55% by weight of the formulation;
the mixture of petrolatum, $C_{16-18}$ fatty alcohols, mineral oil, a glyceride, and a silicone oil comprises from 20% to 27% by weight of the formulation;
the mixture of a glyceryl fatty ester and a sorbitan fatty ester comprises from 3% to 5% by weight of the formulation;
the polysaccharide comprises from 0.3 to 0.5% by weight of the formulation; and
the mixture of an alkylene glycol and a polyalkylene glycol comprises from 20% to 25% by weight of the formulation.

12. The formulation according to claim 11, wherein:
the petroleum is white petrolatum;
the $C_{16-18}$ fatty alcohols are a mixture of cetyl alcohol and stearyl alcohol;
the mineral oil is light mineral oil;
the glyceride is medium chain triglycerides;
the silicone oil is dimethicone;
the glyceryl fatty ester is glyceryl stearate;
the sorbitan fatty ester is polysorbate 20;
the polysaccharide is xanthan gum;
the alkylene glycol is propylene glycol; and
the polyalkylene glycol is polyethylene glycol.

13. The formulation according to claim 11, wherein:
the petroleum is white petrolatum;
the $C_{16-18}$ fatty alcohols are a mixture of cetyl alcohol and stearyl alcohol;
the mineral oil is light mineral oil;
the glyceride is medium chain triglycerides;
the silicone oil is dimethicone;
the glyceryl fatty ester is glyceryl stearate SE;
the sorbitan fatty ester is polysorbate 20;
the polysaccharide is xanthan gum;
the alkylene glycol is propylene glycol; and
the polyalkylene glycol is polyethylene glycol 200.

14. The formulation according to claim 12, further comprising:
a chelating agent component; and
from 0.05% to 3% by weight of the formulation of an antimicrobial preservative component.

15. The formulation of claim 13, further comprising:
0.1% by weight of the formulation of methyl paraben;
0.05% by weight of the formulation of propyl paraben;
0.05% by weight of the formulation of edetate disodium; and
0.5% by weight of the formulation of phenoxyethanol.

16. The formulation of claim 1, wherein the (R)-3-cyclopentyl-3-[4-(7H-pyrrolo [2,3-d] pyrimidin-4-yl)-1H-pyrazol-1-yl] propanenitrile phosphoric acid salt is present in an amount from 0.5% to 1% by weight of the formulation on a free base basis.

17. A pharmaceutical formulation for topical skin application, wherein the formulation is an oil-in-water emulsion, the formulation comprising:
45% to 55% by weight of the formulation of water;
7% by weight of the formulation of a petrolatum;
4.75% by weight of the formulation of $C_{16-18}$ fatty alcohols;
4% by weight of the formulation of a mineral oil;
5% by weight of the formulation of a glyceride;
1% by weight of the formulation of a silicone oil;
3% by weight of the formulation of a glyceryl fatty ester;
1.25% by weight of the formulation of a sorbitan fatty ester;
0.4% by weight of the formulation of a polysaccharide;
15% by weight of the formulation of an alkylene glycol;
7% by weight of the formulation of a polyalkylene glycol; and
from 0.5%-1.5% of (R)-3-cyclopentyl-3-[4-(7H-pyrrolo [2,3-d] pyrimidin-4-yl)-1H-pyrazol-1-yl] propanenitrile phosphoric acid salt by weight of the formulation on a free base basis.

18. The formulation of claim 17, further comprising:
0.1% by weight of the formulation of methyl paraben;
0.05% by weight of the formulation of propyl paraben;
0.05% by weight of the formulation of edetate disodium; and
0.5% by weight of the formulation of phenoxyethanol.

19. The formulation of claim 17, wherein the (R)-3-cyclopentyl-3-[4-(7H-pyrrolo [2,3-d] pyrimidin-4-yl)-1H-pyrazol-1-yl] propanenitrile phosphoric acid salt is present in an amount from 0.5% to 1% by weight of the formulation on a free base basis.

20. A pharmaceutical formulation for topical skin application, wherein the formulation is an oil-in-water emulsion, the formulation comprising:
45% to 55% by weight of the formulation of water;
7% by weight of the formulation of white petrolatum;
3% by weight of the formulation of cetyl alcohol;
1.75% by weight of the formulation of stearyl alcohol;

4% by weight of the formulation of light mineral oil;
5% by weight of the formulation of medium chain triglycerides;
1% by weight of the formulation of dimethicone;
3% by weight of the formulation of glyceryl stearate;
1.25% by weight of the formulation of polysorbate 20;
0.4% by weight of the formulation of xanthan gum;
15% by weight of the formulation of propylene glycol;
7% by weight of the formulation of polyethylene glycol; and
from 0.05% to 1.5% of (R)-3-cyclopentyl-3-[4-(7H-pyrrolo [2,3-d] pyrimidin-4-yl)-1H-pyrazol-1-yl] propanenitrile phosphoric acid salt by weight of the formulation on a free base basis.

21. The formulation of claim 20, further comprising:
0.1% by weight of the formulation of methyl paraben;
0.05% by weight of the formulation of propyl paraben;
0.05% by weight of the formulation of edetate disodium; and
0.5% by weight of the formulation of phenoxyethanol.

22. The formulation of claim 20, wherein the (R)-3-cyclopentyl-3-[4-(7H-pyrrolo [2,3-d] pyrimidin-4-yl)-1H-pyrazol-1-yl] propanenitrile phosphoric acid salt is present in an amount from 0.5% to 1% by weight of the formulation on a free base basis.

23. The formulation of claim 2, wherein the oil-in-water emulsion has a pH of not greater than 3.6.

* * * * *